United States Patent
Yamaguchi et al.

(10) Patent No.: US 9,260,459 B2
(45) Date of Patent: Feb. 16, 2016

(54) 4,6-HEXADECADIENE-2,4-DICARBOXYLIC ACID DERIVATIVE

(71) Applicant: Kyowa Hakko Kirin Co., Ltd., Chiyoda-ku (JP)

(72) Inventors: Shimpei Yamaguchi, Chiyoda-Ku (JP); Yumiko Uochi, Chiyoda-Ku (JP); Tsutomu Agatsuma, Chiyoda-Ku (JP); Susumu Iwamoto, Chiyoda-Ku (JP); Hideyuki Onodera, Chiyoda-Ku (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 14/409,308

(22) PCT Filed: Jun. 25, 2013

(86) PCT No.: PCT/JP2013/067297
§ 371 (c)(1),
(2) Date: Dec. 18, 2014

(87) PCT Pub. No.: WO2014/002967
PCT Pub. Date: Jan. 3, 2014

(65) Prior Publication Data
US 2015/0183809 A1 Jul. 2, 2015

(30) Foreign Application Priority Data
Jun. 25, 2012 (JP) .................... 2012-141849

(51) Int. Cl.
*C07C 69/602* (2006.01)
*C07F 9/141* (2006.01)
*C07C 69/675* (2006.01)
*C07C 57/13* (2006.01)
*C07C 69/708* (2006.01)
*C07C 235/76* (2006.01)
*A61K 31/231* (2006.01)
*C07D 307/33* (2006.01)
*C12R 1/645* (2006.01)
*C07C 233/46* (2006.01)

(52) U.S. Cl.
CPC .............. *C07F 9/141* (2013.01); *A61K 31/231* (2013.01); *C07C 57/13* (2013.01); *C07C 69/602* (2013.01); *C07C 69/675* (2013.01); *C07C 69/708* (2013.01); *C07C 233/46* (2013.01); *C07C 235/76* (2013.01); *C07D 307/33* (2013.01); *C12R 1/645* (2013.01)

(58) Field of Classification Search
None
See application file for complete search history.

(56) References Cited

U.S. PATENT DOCUMENTS

| | | | |
|---|---|---|---|
| 3,501,566 A | 3/1970 | Burkholder et al. | |
| 5,932,613 A * | 8/1999 | Jiang | A61K 31/231 514/510 |
| 2005/0009894 A1 | 1/2005 | Babin et al. | |
| 2006/0276497 A1 | 12/2006 | Chatterjee et al. | |
| 2010/0016354 A1 | 1/2010 | Honda et al. | |

FOREIGN PATENT DOCUMENTS

JP 50081863 A 7/1975

OTHER PUBLICATIONS

Sassa et al. "Structure of Radiclonic Acid, a New Plant Growth-Regulator Produced by a Fungus." *Tetrahed. Lett.* 14.23(1973):2333-2334.
Seto et al. "Studies on the Biosynthesis of Radiclonic Acid." *Tetrahed. Lett.* 18.47(1977):4083-4084.

* cited by examiner

*Primary Examiner* — Yevegeny Valenrod
(74) *Attorney, Agent, or Firm* — Mintz Levin Cohn Ferris Glovsky and Popeo, P.C.; David G. Conlin; Christopher R. Cowles

(57) ABSTRACT

A 4,6-hexadecadiene-2,4-dicarboxylic acid derivative represented by the following general formula (1) or a pharmaceutically acceptable salt thereof, each of which has an antitumor activity, and the like, are provided.

(I)

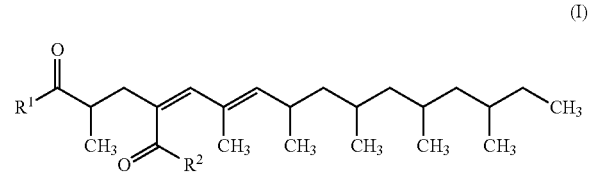

[wherein, $R^1$ represents hydroxy, —$OR^3$ (wherein $R^3$ represents optionally substituted lower alkyl or an optionally substituted aliphatic heterocyclic group), or —$NR^4R^5$ (wherein $R^4$ and $R^5$ may be the same or different, and each represents a hydrogen atom or optionally substituted lower alkyl) and $R^2$ represents hydroxy or —$OR^6$ (wherein $R^6$ represents optionally substituted lower alkyl or optionally substituted aralkyl)].

18 Claims, No Drawings

4,6-HEXADECADIENE-2,4-DICARBOXYLIC ACID DERIVATIVE

This application is the U.S. national stage pursuant to 35 U.S.C. §371, of Japanese international application Ser. No. PCT/JP2013/067297, filed Jun. 25, 2013, designating the United States and published in English on Jan. 3, 2014 as publication WO 2014/002967A1, which claims priority to Japanese application Ser. No. 2012-141849, filed Jun. 25, 2012. The entire contents of the aforementioned patent applications are incorporated herein by this reference.

TECHNICAL FIELD

The present invention relates to a 4,6-hexadecadiene-2,4-dicarboxylic acid derivative or a pharmaceutically acceptable salt thereof, each of which has an anti-tumor activity, and the like.

BACKGROUND ART

In cancer chemotherapy, various types of anti-tumor agents including drugs acting on microtubules such as taxanes and vinca alkaloids, topoisomerase inhibitors, alkylating agents, and the like have been used. However, these agents have problems that an adverse effect such as myelotoxicity or neurological disorder or drug resistance emerges, and therefore, a novel anti-tumor agent in which these problems are solved is always demanded.

On the other hand, a plant growth regulator having a 4,6-hexadecadiene-2,4-dicarboxylic acid structure is known (Patent Document 1, Non-Patent Document 1 and 2).

PRIOR ART DOCUMENT

Patent Document

Patent Document 1: Japanese Published Unexamined Patent Application No. S50-81863

Non-Patent Document

Non-Patent Document 1: Tetrahedron Letters, 1973, vol. 14, No. 23, pp. 2333-2334

Non-Patent Document 2: Tetrahedron Letters, 1977, vol. 18, No. 47, pp. 4083-4084

DISCLOSURE OF INVENTION

Problem that the Invention is to Solve

An object of the present Invention is to provide a 4,6-hexadecadiene-2,4-dicarboxylic acid derivative or a pharmaceutically acceptable salt thereof, each of which has an anti-tumor activity, and the like.

Means for Solving the Problem

The present invention relates to the following (1) to (40).

(1) A 4,6-hexadecadiene-2,4-dicarboxylic acid derivative represented by the general formula (I) or a pharmaceutically acceptable salt thereof.

[Chemical Formula 1]

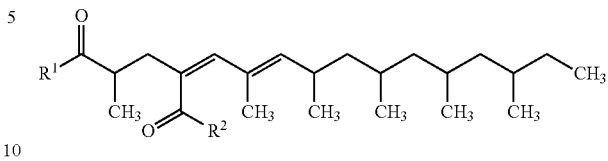

(I)

[wherein, $R^1$ represents hydroxy, —$OR^3$ (wherein $R^3$ represents optionally substituted lower alkyl or an optionally substituted aliphatic heterocyclic group), or —$NR^4R^5$ (wherein $R^4$ and $R^5$ may be the same or different, and each represents a hydrogen atom or optionally substituted lower alkyl) and $R^2$ represents hydroxy or —$OR^6$ (wherein $R^6$ represents optionally substituted lower alkyl or optionally substituted aralkyl)]

(2) The 4,6-hexadecadiene-2,4-dicarboxylic acid derivative or a pharmaceutically acceptable salt thereof according to the above (1), wherein $R^2$ is hydroxy.

(3) The 4,6-hexadecadiene-2,4-dicarboxylic acid derivative or a pharmaceutically acceptable salt thereof according to the above (1), wherein $R^2$ is —$OR^6$ (wherein $R^6$ represents optionally substituted lower alkyl or optionally substituted aralkyl).

(4) The 4,6-hexadecadiene-2,4-dicarboxylic acid derivative or a pharmaceutically acceptable salt thereof according to the above (3), wherein $R^6$ is optionally substituted lower alkyl.

(5) The 4,6-hexadecadiene-2,4-dicarboxylic acid derivative or a pharmaceutically acceptable salt thereof according to the above (3), wherein $R^6$ is substituted lower alkyl.

(6) The 4,6-hexadecadiene-2,4-dicarboxylic acid derivative or a pharmaceutically acceptable salt thereof according to the above (3) wherein $R^6$ is acetoxymethyl.

(7) The 4,6-hexadecadiene-2,4-dicarboxylic acid derivative or a pharmaceutically acceptable salt thereof according to any one of the above (1) to (6), wherein $R^1$ is hydroxy.

(8) The 4,6-hexadecadiene-2,4-dicarboxylic acid derivative or a pharmaceutically acceptable salt thereof according to any one of the above (1) to (6), wherein $R^1$ is —$OR^3$ (wherein $R^3$ represents optionally substituted lower alkyl or an optionally substituted aliphatic heterocyclic group).

(9) The 4,6-hexadecadiene-2,4-dicarboxylic acid derivative or a pharmaceutically acceptable salt thereof according to the above (8), wherein $R^3$ is an optionally substituted aliphatic heterocyclic group.

(10) The 4,6-hexadecadiene-2,4-dicarboxylic acid derivative or a pharmaceutically acceptable salt thereof according to the above (8), wherein $R^3$ is optionally substituted tetrahydrofuranyl.

(11) The 4,6-hexadecadiene-2,4-dicarboxylic acid derivative or a pharmaceutically acceptable salt thereof according to the above (6), wherein $R^3$ is optionally substituted oxotetrahydrofuranyl.

(12) The 4,6-hexadecadiene-2,4-dicarboxylic acid derivative or a pharmaceutically acceptable salt thereof according to the above (8), wherein $R^3$ is oxotetrahydrofuranyl substituted with carboxy.

(13) The 4,6-hexadecadiene-2,4-dicarboxylic acid derivative or a pharmaceutically acceptable salt thereof according to the above (8), wherein $R^3$ is optionally substituted lower alkyl.

(14) The 4,6-hexadecadiene-2,4-dicarboxylic acid derivative or a pharmaceutically acceptable salt thereof according to the above (8), wherein $R^3$ is substituted lower alkyl.

(15) The 4,6-hexadecadiene-2,4-dicarboxylic acid derivative or a pharmaceutically acceptable salt thereof according to the above (8), wherein R³ is substituted propyl.

(16) A 4,6-hexadecadiene-2,4-dicarboxylic acid derivative selected from 4-{(4Z,6E)-4-carboxy-2,6,8,10,12,14-hexamethylhexadec-4,6-dienoyloxy}-5-oxotetrahydrofuran-2,3-dicarboxylic acid and 1-{(4Z,6E)-4-carboxy-2,6,8,10,12,14-hexamethylhexadec-4,6-dienoyloxy}-3-hydroxypropane-1,2,3-tricarboxylic acid, or a pharmaceutically acceptable salt thereof.

(17) A pharmaceutical composition comprising, as an active ingredient, the 4,6-hexadecadiene-2,4-dicarboxylic acid derivative or a pharmaceutically acceptable salt thereof described in any one of the above (1) to (16).

(18) An anti-tumor agent comprising, as an active ingredient, the 4,6-hexadecadiene-2,4-dicarboxylic acid derivative or a pharmaceutically acceptable salt thereof described in any one of the above (1) to (16).

(19) A method for treating a tumor comprising a step of administering an effective amount of the 4,6-hexadecadiene-2,4-dicarboxylic acid derivative or a pharmaceutically acceptable salt thereof described in any one of the above (1) to (16).

(20) The 4,6-hexadecadiene-2,4-dicarboxylic acid derivative or a pharmaceutically acceptable salt thereof described in any one of the above (1) to (16) for use in the treatment of a tumor.

(21) Use of the 4,6-hexadecadiene-2,4-dicarboxylic acid derivative or a pharmaceutically acceptable salt thereof described in any one of the above (1) to (16) for the manufacture of an anti-tumor agent.

(22) A compound produced by a *Scopulariopsis* sp. CPM1007 strain or a pharmaceutically acceptable salt thereof.

(23) 4-{(4Z,6E)-4-carboxy-2,6,8,10,12,14-hexamethylhexadec-4,6-dienoyloxy}-5-oxotetrahydrofuran-2,3-dicarboxylic acid produced by a *Scopulariopsis* sp. CPM1007 strain.

(24) (Z)-2-methyl-4-{(E)-2,4,6,8,10-pentamethyldodec-2-enylidene}pentanedicarboxylic acid produced by a *Scopulariopsis* sp. CPM1007 strain.

(25) An anti-tumor agent comprising, as an active ingredient, a compound produced by a *Scopulariopsis* sp. CPM1007 strain or a pharmaceutically acceptable salt thereof.

(26) The anti-tumor agent according to the above (25), wherein the compound produced by a *Scopulariopsis* sp. CPM1007 strain is 4-{(4Z,6E)-4-carboxy-2,6,8,10,12,14-hexamethylhexadec-4,6-dienoyloxy}-5-oxotetrahydrofuran-2,3-dicarboxylic acid.

(27) The anti-tumor agent according to the above (25), wherein the compound produced by a *Scopulariopsis* sp, CPM100 strain is (Z)-2-methyl-4-{(E)-2,4,6,8,10-pentamethyldodec-2-enylidene}pentanedicarboxylic acid.

(28) A method for treating a tumor comprising a step of administering an effective amount of a compound produced by a *Scopulariopsis* sp, CPM1007 strain or a pharmaceutically acceptable salt thereof.

(29) The method for treating according to the above (28), wherein the compound produced by a *Scopulariopsis* sp. CPM1007 strain is 4-{(4Z,6E)-4-carboxy-2,6,8,10,12,14-hexamethylhexadec-4,6-dienoyloxy}-5-oxotetrahydrofuran-2,3-dicarboxylic acid.

(30) The method for treating according to the above (28), wherein the compound produced by a *Scopulariopsis* sp. CPM1007 strain is (Z)-2-methyl-4-{((E)-2,4,6,8,10-pentamethyldodec-2-enylidene}pentanedicarboxylic acid.

(31) A compound produced by a *Scopulariopsis* sp. CPM1007 strain or a pharmaceutically acceptable salt thereof for use in the treatment of a tumor.

(32) The compound or a pharmaceutically acceptable salt thereof according to the above (31), wherein the compound produced by a *Scopulariopsis* sp. CPM1007 strain is 4-{(4Z,6E)-4-carboxy-2,6,8,10,12,14-hexamethylhexadec-4,6-dienoyloxy}-5-oxotetrahydrofuran-2,3-dicarboxylic acid.

(33) The compound or a pharmaceutically acceptable salt thereof according to the above (31), wherein the compound produced by a *Scopulariopsis* sp. CPM1007 strain is (Z)-2-methyl-4-{(E)-2,4,6,8,10-pentamethyldodec-2-enylidene}pentanedicarboxylic acid.

(34) Use of a compound produced by a *Scopulariopsis* sp. CPM1007 strain or a pharmaceutically acceptable salt thereof for the manufacture of an anti-tumor agent.

(35) The use according to the above (34), wherein the compound produced by a *Scopulariopsis* sp. CPM1007 strain is 4-{(4Z,6E)-4-carboxy-2,6,8,10,12,14-hexamethylhexadec-4,6-dienoyloxy}-5-oxotetrahydrofuran-2,3-dicarboxylic acid.

(36) The use according to the above (34), wherein the compound produced by a *Scopulariopsis* sp. CPM1007 strain is (Z)-2-methyl-4-{(E)-2,4,6,8,10-pentamethyldodec-2-enylidene}pentanedicarboxylic acid.

(37) A *Scopulariopsis* sp. CPM1007 strain.

(38) A *Scopulariopsis* sp. CPM1007 strain, which produces the 4,6-hexadecadiene-2,4-dicarboxylic acid derivative or a pharmaceutically acceptable salt thereof described in any one of the above (1) to (16).

(39) A *Scopulariopsis sp. CPM*1007 strain, which produces 4-{(4Z,6E)-4-carboxy-2,6,8,10,12,14-hexamethylhexadec-4,6-dienoyloxy}-5-oxotetrahydrofuran-2,3-dicarboxylic acid or a pharmaceutically acceptable salt thereof.

(40) A *Scopulariopsis* sp. CPM1007 strain, which produces (Z)-2-methyl-4-{(E)-2,4,6,8,10-pentamethyldodec-2-enylidene}pentanedicarboxylic acid or a pharmaceutically acceptable salt thereof.

Effects of Invention

The 4,6-hexadecadiene-2,4-dicarboxylic acid derivative of the present invention can be utilized as, for example, a therapeutic agent for a tumor. According to the present invention, a 4,6-hexadecadiene-2,4-dicarboxylic acid derivative or a pharmaceutically acceptable salt thereof, each of which has an anti-tumor activity, and the like are provided.

MODE FOR CARRYING OUT THE INVENTION

Hereinafter, a compound, represented by the general formula (I) is referred to as Compound (I). The compounds having the other formula numbers are referred to in the same manner.

In the definition of each group in the general formula (I), examples of the lower alkyl include linear or branched alkyl having 1 to 10 carbon atoms, and more specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, and the like.

Examples of the aralkyl include aralkyl having 7 to 16 carbon atoms, and more specific examples thereof include benzyl, phenetyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl, and the like.

Examples of the aliphatic heterocyclic group include 5- to 7-membered monocyclic aliphatic heterocyclic groups which contain at least one atom selected from a nitrogen atom, an oxygen atom, and a sulfur atom, bicyclic or tricyclic aliphatic heterocyclic groups, in which 3- to 8-membered rings are fused, and which contain at least one atom selected from a nitrogen atom, an oxygen atom, and a sulfur atom, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, oxotetrahydrofuranyl, 4,5-dihydro-1,3-thiazolyl, tetrahydro-2H-pyranyl, 5,6-dihydro-2H-pyranyl, oxazolindinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, and the like.

Examples of the substituents in the optionally substituted lower alkyl and the optionally substituted aralkyl, which may be the same or different and in number of a substitutable number, preferably in number of 1 to 4, include substituents selected from the group comprising halogen, hydroxy, mercapto, nitro, cyano, carboxy, carbamoyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^xR^y$ (wherein $R^x$ and $R^y$ may be the same or different, and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl, and the like), $C_{2-11}$ alkanoyl, $C_{7-15}$ aroyl, optionally substituted $C_{1-10}$ alkoxycarbonyl (examples of the substituent of the substituted $C_{1-10}$ alkoxycarbonyl include 1 to 3 substituent(s) such as $C_{2-11}$ alkanoyloxy, and the like), $C_{6-14}$ aryloxycarbonyl, $C_{1-10}$ alkylcarbamoyl, di-$C_{1-10}$ alkylcarbamoyl, di-$C_{1-10}$ alkoxyphosphoryloxy, optionally substituted $C_{7-16}$ aralkyloxycarbonyl (examples of the substituent of the substituted $C_{7-16}$ aralkyloxycarbonyl include 1 to 3 substituent(s) such as $C_{2-11}$ alkanoyloxy, and the like), and the like. Preferred examples of the substituents include hydroxy, carboxy, $C_{1-10}$ alkoxycarbonyl, and the like.

Examples of the substituents in the optionally substituted aliphatic heterocyclic group, which may be the same or different and in number of a substitutable number, preferably in number of 1 to 4, include substituents selected from the group comprising oxo, halogen, hydroxy, mercapto, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy, cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{Xb}R^{Yb}$ (wherein $R^{Xb}$ and $R^{Yb}$ may be the same or different, and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl, and the like), $C_{2-11}$ alkanoyl, $C_{7-15}$ aroyl, optionally substituted $C_{1-10}$ alkoxycarbonyl (examples of the substituent of the substituted $C_{1-10}$ alkoxycarbonyl include 1 to 3 substituent(s) such as $C_{2-11}$ alkanoyloxy, and the like), $C_{6-14}$ aryloxycarbonyl, $C_{1-10}$ alkylcarbamoyl, di-$C_{1-10}$ alkylcarbamoyl, optionally substituted $C_{7-16}$ aralkyloxycarbonyl (examples of the substituent of the substituted $C_{7-16}$ aralkyloxycarbonyl include 1 to 3 substituent(s) such as $C_{2-11}$ alkanoyloxy, and the like), and the like. Preferred examples of the substituents include hydroxy, carboxy, $C_{1-10}$ alkoxycarbonyl, and the like.

Examples of the $C_{1-10}$ alkyl and the alkyl moiety of the $C_{1-10}$ alkoxy, the $C_{1-10}$ alkoxycarbonyl, the $C_{1-10}$ alkylthio, the $C_{1-10}$ alkylcarbamoyl, the di-$C_{1-10}$ alkylcarbamoyl, the $C_{2-11}$ alkanoyl, the $C_{2-11}$ alkanoyloxy, and the $C_{1-10}$ alkoxyphosphoryloxy shown here include the groups exemplified for the lower alkyl described above.

Examples of the $C_{3-8}$ cycloalkyl and the cycloalkyl moiety of the $C_{3-8}$ cycloalkoxy include cycloalkyl having 3 to 8 carbon atoms, and more specific examples thereof include cyclopropyl, cyclobutyl, cyclopentyl, cyclohexyl, cycloheptyl, cyclooctyl, and the like.

Examples of the $C_{6-14}$ aryl and the aryl moiety of the $C_{6-14}$ aryloxy, the $C_{7-15}$ aroyl, the $C_{7-15}$ aroyloxy, and the $C_{6-14}$ aryloxycarbonyl include aryl having 6 to 14 carbon atoms, and more specific examples thereof include phenyl, naphthyl, azulenyl, anthryl, and the like.

Further, examples of the $C_{7-16}$ aralkyl and the aralkyl moiety of the $C_{7-16}$ is aralkyloxy and the $C_{7-16}$ aralkyloxycarbonyl shown here include the groups exemplified for the aralkyl described above.

Further, examples of the aliphatic heterocyclic group shown here include the groups exemplified for the aliphatic heterocyclic group described above.

Examples of the aromatic heterocyclic group include 5- or 6-membered monocyclic aromatic heterocyclic groups which contain at least one atom selected from a nitrogen atom, an oxygen atom, and a sulfur atom, bicyclic or tricyclic aromatic heterocyclic groups, in which 3- to 8-membered rings are fused, and which contain at least one atom selected from a nitrogen atom, an oxygen atom, and a sulfur atom, and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimdinyl, imidazopyridinyl, purinyl, quinolinyl, isoquinolinyl, cinnolinyl, phthalzainyl, quinazolinyl, quinoxalinyl, naphthyridinyl, and the like.

The halogen means each atom of fluorine, chlorine, bromine, or iodine.

The pharmaceutically acceptable salt of Compound (I) includes, for example, pharmaceutically acceptable acid addition salts, metal salts, ammonium salts, organic amine addition salts, amino acid, addition salts, and the like. Examples of the pharmaceutically acceptable acid addition salts of Compound (I) include inorganic acid salts such as hydrochlorides, hydrobromides, nitrates, sulfates, and phosphates, organic acid salts such as acetates, oxalates, maleates, fumarates, citrates, benzoates, methanesulfonates, and the like. Examples of the pharmaceutically acceptable metal salts include alkali metal salts such as sodium salts, potassium, salts, and the like, alkaline earth metal salts such as magnesium salts, calcium salts, and the like, aluminum salts, zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of lysine, glycine, phenylalanine, aspartic acid, glutamic acid, and the like.

Next, product ion methods of Compound (I) are explained.

In the production methods shown below, when the defined groups change under the conditions of the production methods or are inappropriate for carrying out the production methods, a target compound can be produced by using methods of the introduction and removal of a protecting group commonly used in the synthetic, organic chemistry (for example, methods described in Protective Groups in Organic Synthesis, 4th edition, written by T. W. Greene, John Wiley & Sons Inc., (1999), and the like) and the like. Further, if necessary, the order of the reaction steps such as introduction of a substituent can be changed.

Production Method 1

Compound 1 and Compound 2 are produced by culturing a microorganism which belongs to the genus *Scopulariopsis* and has an ability to produce Compound 1 and Compound 2, and producing and accumulating Compound 1 and Compound 2, and then, collecting Compound 1 and Compound 2 from the culture.

As the microorganism having an ability to produce Compound 1 and Compound 2, any strain can be used as long as it is a strain which belongs to the genus *Scopulariopsis* and has an ability to produce Compound 1 and Compound 2. Further, a mutant strain obtained by mutating such a strain by an artificial mutation method, for example, UV irradiation, X-ray irradiation, a treatment with a mutagen, or the like, or a spontaneous mutant strain can be used in the present invention as long as it has an ability to produce Compound 1 and Compound 2. Specific examples thereof include, for example, a *Scopulariopsis* sp. CPM1007 strain (hereinafter abbreviated as CPM1007 strain).

The CPM1007 strain used in the present invention is a strain isolated from soil. Based on the mycological characteristics, it has been revealed that the strain belongs to the genus *Scopulariopsis* in the class Hyphomycetes, and the *Scopulariopsis* sp. CPM1007 strain has been deposited in the National Institute of Technology and Evaluation (NITE) Patent Microorganisms Depositary (NPMD) (2-5-8, Kazusakamatari, Kisarazu-shi, Chiba-ken, 292-0818, Japan)) under Budapest Treaty on Jun. 15, 2012 as the accession number of MITE BP-1377. The mycological characteristics of the strain are as follows.

(I) Macroscopic Observation

In the case where the CPM1007 strain is cultured at 25° C. on an agar medium of malt extract, the diameter of the colony reaches 10 to 13 mm on day 14 after the start of the cultivation. The front side surface of the colony is woolly in appearance and its color is dark grayish yellow, and the color of the back side surface of the colony is the same as that of the front side surface or white. In the case where the CPM1007 strain is cultured at 25° C. on an agar medium of cornmeal, the diameter of the colony reaches 18 to 24 mm on day 14 after the start of the cultivation. The front side surface of the colony is velvety in appearance and its color is dark grayish yellow green, and the color of the back side surface of the colony is the same as that of the front side surface.

(II) Microscopic Observation

The hyphae of the CPM1007 strain have septa and branch well. In many cases, the conidiogenous cells of the CPM1007 strain are formed singly from substrate hyphae and aerial hyphae, but in rare cases, one to three conidiogenous cells are formed on a branched conidiophore from a vegetative hypha. The conidiogenous cells of the CPM1007 strain have the following characteristics: the cell has an ampoule shape, the total length is from 5 to 12 μm, the width of the basal portion at a swollen part is from 2.4 to 3.0 μm, and the width of the tip portion is from 0.8 to 1.2 μm. The conidia of the CPM1007 strain are formed at the tip of the conidiogenous cells in the annello type conidial ontogeny.

The conidia of the CPM1007 strain are linked in a chain, and have the following characteristics: the conidia are single cells in the form of an oval to obovate, the basal portion is flat, the color is brown, the long diameter is from 4.2 to 5.0 μm, and the short diameter is from 3.0 to 4.0 μm. Some conidia of the CPM1007 strain have a transparent thin film therearound.

In this strain, only the above-described anamorph was observed, and a teleomorph was not observed.

Based on the above-described mycological characteristics, with respect to the taxonomic position, this strain belongs to the genus *Scopulariopsis* in the class Hyphomycetes according to "The Genera of Fungi Sporulating in Pure Culture, 2nd ed., Cramer, Vaduz, J. A. von Arx (1974)".

As the culture medium for culturing the microorganism which produces the compound of the present invention, either a synthetic medium or a natural medium can be used as long as it is a medium which properly contains a carbon source, a nitrogen source, inorganic salts, and the like which can be assimilated by the microorganism.

As the carbon source, glucose, starch, dextrin, sucrose, lactose, molasses, and the like are used alone or in combination with one another.

As the nitrogen source, ammonium sulfate, sodium nitrate, peptone, meat extract, yeast extract, dry yeast, corn steep liquor, soybean powder, and the like are used alone or in combination with one another.

Other than these, if necessary, inorganic salts such as sodium chloride, potassium chloride, magnesium sulfate, calcium carbonate, potassium dihydrogen phosphate, manganese sulfate, zinc sulfate, copper sulfate, and the like, are added.

As is seen in the other fungi, the properties of the CPM1007 strain easily change. For example, the CPM1007 strain, or even a spontaneous or induced mutant strain, a transfectant, and a recombinant derived from this strain can all be used in the present invention as long as they produce the compound of the present invention.

As the culture method, a liquid culture method, a solid culture method, or the like under aerobic conditions can be used. The compound of the present invention can be produced by cultivation at a temperature of 20 to 30° C., preferably at a temperature around 25° C., for 4 to 21 days. It is desirable to stop the cultivation when the produced amount of the compound of the present invention has reached the maximum in the culture.

Examples of a method for isolating and purifying the compound of the present invention accumulated in the culture broth from the culture broth include a method commonly used for isolating and purifying a common microbial metabolite from a culture broth. Specifically, the target compound is extracted by directly adding methanol, ethanol, 2-propanol, acetone, or the like to the culture, or the target compound is extracted by carrying out a two layer partition extraction with 2-butanone, tert-butanol, n-butanol, or the like. Alternatively, the culture is separated into a culture filtrate and microbial cells by filtration, and further, a microbial cell component is extracted with a solvent such as chloroform, acetone, or methanol from the microbial cells. The obtained extract solution and/or culture filtrate is, for example, passed through a column filled with a polystyrene-based adsorbent such as Diaion HP-20 or HP-20ss (manufactured by Mitsubishi Chemical Corporation), or the like, to adsorb 1 the target compound, followed by elution with methanol, acetone, or the like. Then, Compound 1 and Compound 2 can be obtained, respectively, by isolation and purification through, for example, gel filtration which uses Sephadex LH-20, TOYOPEARL KW 40, or the like, column chromatography which uses an octadecyl group-bound silica gel (ODS) or the like, high performance liquid chromatography, silica gel column chromatography, or the like.

Production Method 2

Compound (I) can be produced by chemically modifying Compound 1 or Compound 2 obtained by the above-described method according to, for example, a known method [for example, a method described in Comprehensive Organic Transformations 2nd edition, written by R. C. Larock, Vch Verlagsgesellschaft Mbh (1999), and the like], and the like.

Production Method 3

Among Compounds (I), Compounds (a-1), (a-2), and (a-3) represented by the following formulae can be produced according to, for example, the following step.

[Chemical Formula 2]
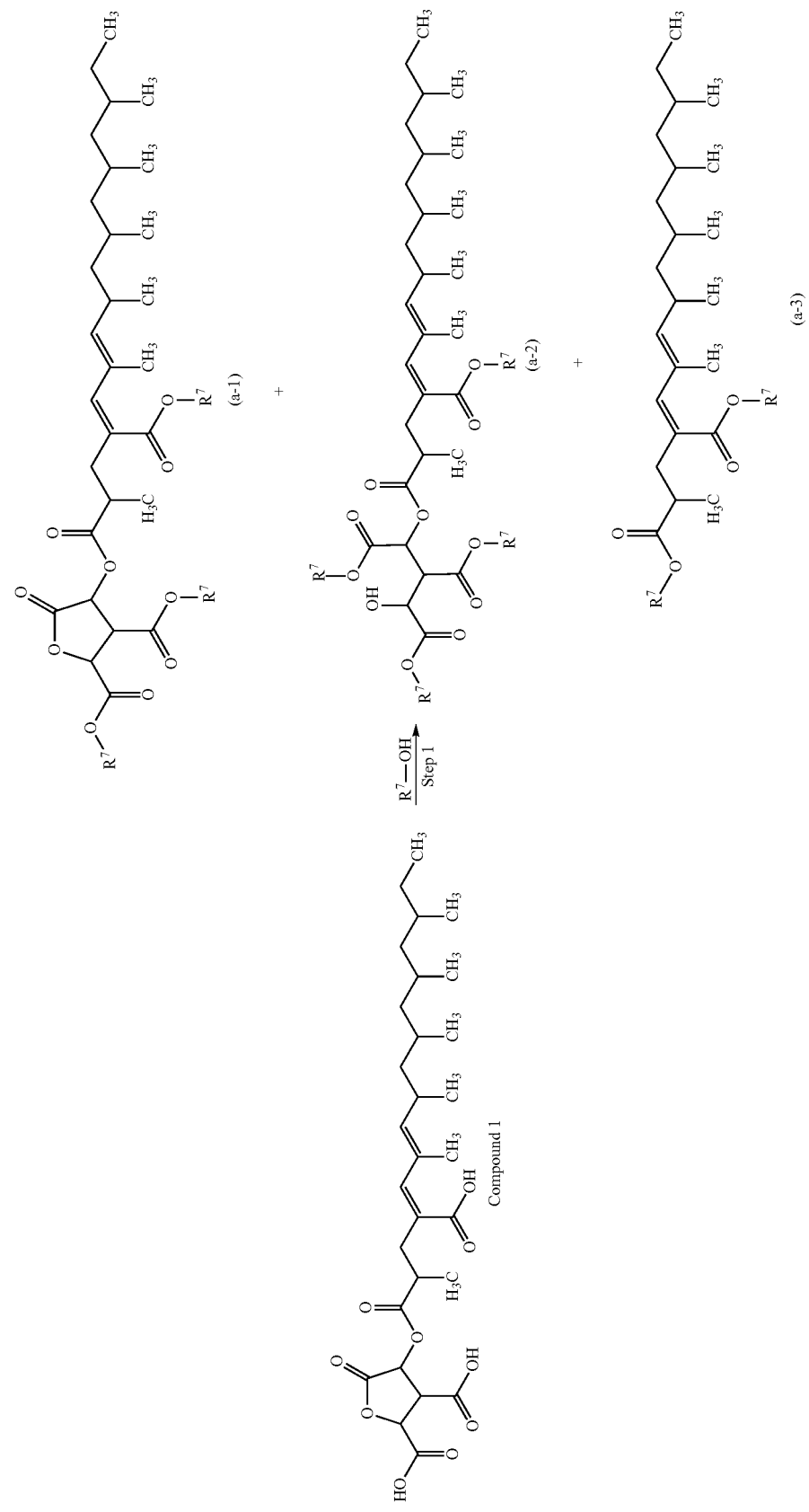

(wherein, $R^7$ represents $C_{1-10}$ alkyl optionally substituted with $C_{2-11}$ alkanoyloxy, or $C_{7-16}$ aralkyl optionally substituted with $C_{2-11}$ alkanoyloxy)

Step 1

Compounds (a-1), (a-2), and (a-3) can be produced as a mixture thereof by reacting Compound 1 obtained by the method described in Example 1 in the presence of 1 equivalent to a large excess amount of $R^7OH$ (wherein $R^7$ has the same definition as described above) and 1 to 10 equivalents of a condensing agent in a solvent at a temperature between $-78°$ C. and the boiling point of the solvent used for 5 minutes to 72 hours. Further, if necessary, it is also possible to carry out the reaction by adding 0.1 to 10 equivalents of an additive. The obtained mixture of Compounds (a-1), (a-2), and (a-3) is subjected to, for example, silica gel chromatography and the like, whereby the respective compounds can be separated and purified.

Examples of the condensing agent include dicyclohexylcarbodiimide (DCC), diisopropylcarbodiimide (DIC), 1-ethyl-3-(3-dimethylaminopropyl) carbodiimide hydrochloride (EDC-HCl), 1,1'-carbonyldiimidazole (CDI), and the like. Examples of the additive include 1,8-diazabicyclo[5,4,0]-7-undecene (DBU), N,N-dimethyl-4-aminopyridine (DMAP) 1-hydroxybenzotriazole, N-hydroxysuccinimide, copper(I) chloride, copper(II) chloride, copper (I) iodide, copper(II) trifluoromethanesulfonate, and the like. Examples of the solvent include water, diethyl ether, 1,2-dimethoxyethane, tetrahydrofuran (THF), 1,4-dioxane, N,N-dimethylformamide (DMF), N,N-dimethylacetamide, dimethyl sulfoxide (DMSO), benzene, toluene, xylene, dichloromethane, chloroform, carbon tetrachloride, 1,2-dichloroethane, acetonitrile, ethyl acetate, methyl acetate, methyl ethyl ketone, hexane, and the like, and these are used alone or as a mixture thereof.

Further, the above esterification reaction can also be carried out by using 1 equivalent to a large excess amount of $R^7$—X (wherein $R^7$ has the same definition as described above and X represents halogen) and 1 to 10 equivalents of a base. Examples of the base include sodium hydride, potassium hydride, lithium hydroxide, sodium hydroxide, potassium hydroxide, sodium carbonate, potassium carbonate, cesium carbonate, sodium hydrogen carbonate, n-butyl lithium, sec-butyl lithium, silver(I) oxide, DBU, DMAP, triethylamine, diisopropylethylamine, pyridine, and the like.

Further, in the case where $R^7$ is methyl, the above-described mixture of Compounds (a-1), (a-2), and (a-3) can also be obtained by carrying out the methyl esterification reaction of Compound 1 using, for example, diazomethane, trimethylsilyldiazomethane, or the like.

Also, depending on the conditions used for the reaction, the production ratio of Compounds (a-1), (a-2), and (a-3) may sometimes vary. Further, depending on the amount of the reagent used for the reaction, a compound in which a part of $R^7$ in Compounds (a-1), (a-2), and (a-3) is replaced by a hydrogen atom may sometimes be obtained.

Production Method 4

Among Compounds (I), Compound (a-6) in which $R^1$ is —$OR^3$ (wherein $R^3$ has the same definition as described above) can be produced according to, for example, the following steps.

[Chemical Formula 3]

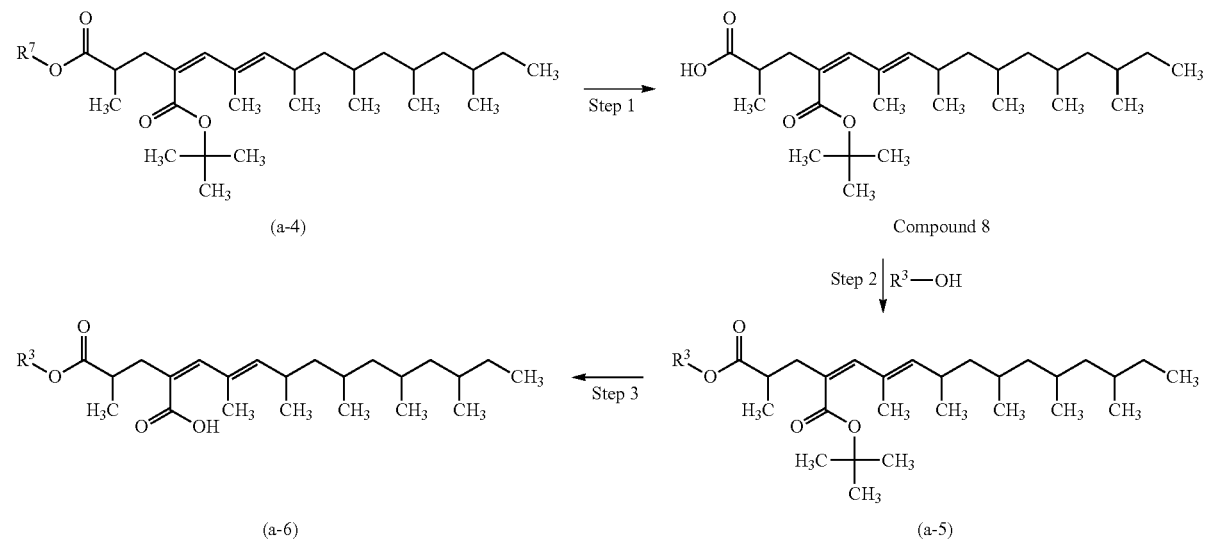

(wherein, $R^3$ and $R^7$ have the same definitions as described above, respectively)

Step 1

Compound 8 can be obtained by reacting Compound (a-4) with 1 to 100 equivalents of a base in a solvent at a temperature between $-78°$ C. and the boiling point of the solvent used for 5 minutes to 72 hours. Examples of the base include lithium hydroxide, sodium hydroxide, potassium hydroxide, and the like, and preferably, 1 to 10 equivalents of sodium hydroxide is used. Examples of the solvent include water, diethyl ether, 1,2-dimethoxyethane, THF, 1,4-dioxane, acetonitrile, methanol, ethanol, 1-propanol, isopropanol, 1-butanol, tert-butanol, and the like, and these are used alone or as a mixture thereof.

Compound (a-4) can be obtained by a method based on Production Method 1.

Step 2

Compound (a-5) can be produced in the same manner as Production Method 1 using Compound 8 and 1 equivalent to a large excess amount of $R^3OH$ (wherein $R^3$ has the same definition as described above).

Step 3

Compound (a-6) can be produced by reacting Compound (a-5) in a solvent in the presence of a catalytic amount to a large excess amount of an acid at a temperature between −78° C. and the boiling point of the solvent used for 5 minutes to 72 hours. Examples of the acid include hydrochloric acid, sulfuric acid, nitric acid, acetic acid, trifluoroacetic acid, formic acid, bromic acid, tosylic acid, and the like. Examples of the solvent include methanol, ethanol, toluene, ethyl acetate, acetonitrile, diethyl ether, THF, 1,2-dimethoxyethane, dioxane, DMF, N-methylpyrrolidone, hexane, water, dichloromethane, chloroform, 1,2-dichloroethane, and the like, and these are used alone or as a mixture thereof.

Production Method 5

Among Compounds (I), Compound (a-8) in which $R^1$ is —$NR^4R^5$ (wherein $R^4$ and $R^5$ have the same definitions as described above, respectively) can be produced according to, for example, the following step.

C. and the boiling point of the solvent used for 5 minutes to 72 hours. Further, if necessary, it is also possible to carry out the reaction by adding 0.1 to 10 equivalents of an additive. Examples of the condensing agent include CDI, DCC, EDC.HCl, and the like, and these are preferably used in an amount of 0.1 to 10 equivalents. Examples of the additive include DBU, DMAP, 1-hydroxybenzotriazole, N-hydroxysuccinimide, and the like, and these are preferably used in an amount of 0.1 to 2 equivalents. Examples of the solvent include water, diethyl ether, 1,2-dimethoxyethane, THF, 1,4-dioxane, DMF, N,N-dimethylacetamide, DMSO, benzene, toluene, xylene, dichloromethane, chloroform, carbon tetrachloride, 1,2-dichloroethane, acetonitrile, ethyl acetate, methyl acetate, methyl ethyl ketone, methanol, ethanol,

[Chemical Formula 4]

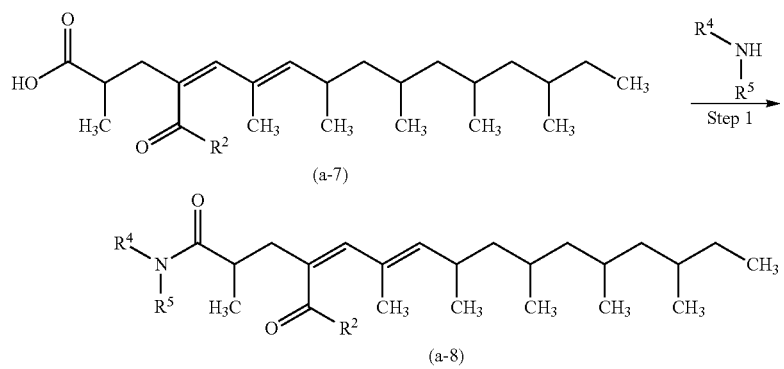

(wherein, $R^2$, $R^4$, and $R^5$ have the same definitions as described above, respectively)

Step 1

Compound (a-8) can be produced by reacting Compound (a-7) in the presence of 1 equivalent to a large excess amount of $R^4R^5NH$ (wherein $R^4$ and $R^5$ have the same definitions as described above, respectively) and 1 to 10 equivalents of a condensing agent, in a solvent, at a temperature between −78°

1-propanol, isopropanol, 1-butanol, tert-butanol, hexane, and the like, and these are used alone or as a mixture thereof.

Compound (a-7) can be obtained by a method based on Step 1 of Production Method 2.

Production Method 6

Among Compounds (I), Compound (a-10) represented by the following formula can be produced according to, for example, the following step.

[Chemical Formula 5]

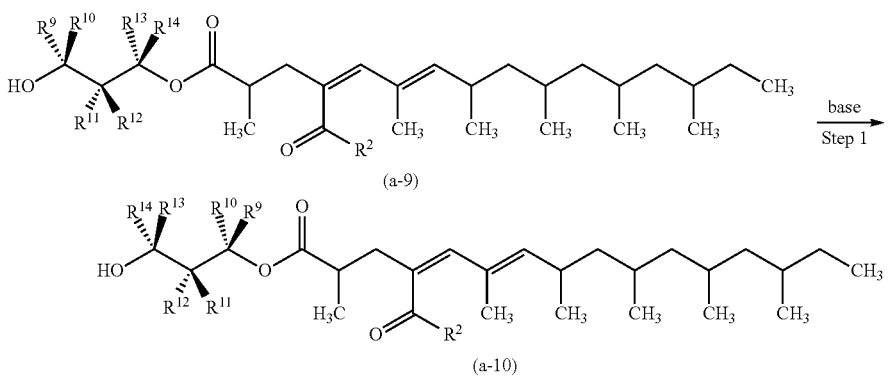

(wherein, $R^2$ has the same definition as described above, and $R^9$, $R^{10}$, $R^{11}$, $R^{12}$, $R^{13}$, and $R^{14}$ may be the same or different, and each represents a hydrogen atom, carboxy, $C_{1-10}$ alkoxycarbonyl optionally substituted with $C_{2-11}$ alkanoyloxy, or $C_{7-16}$ aralkyloxycarbonyl optionally substituted with $C_{2-11}$ alkanoyloxy)

Step 1

Compound (a-10) can be produced, by reacting Compound (a-9) in the presence of a catalytic amount to a large excess amount of a base, in a solvent, at a temperature between $-78°$ C. and the boiling point of the solvent used for 5 minutes to 72 hours.

Examples of the base include sodium carbonate, potassium carbonate, cesium carbonate, potassium hydrogen phosphate, potassium dihydrogen phosphate, sodium hydrogen phosphate, sodium dihydrogen phosphate, and the like. Examples of the solvent include water, acetone, diethyl ether, 1,2-dimethoxyethane, THF, 1,4-dioxane, DMF, N,N-dimethylacetamide, DMSO, benzene, toluene, xylene, dichloromethane, chloroform, carbon tetrachloride, 1,2-dichloroethane, acetonitrile, ethyl acetate, methyl acetate, methyl ethyl ketone, methanol, ethanol, 1-propanol, isopropanol, 1-butanol, tert-butanol, hexane, and the like, and these are used alone or as a mixture thereof.

Compound (a-9) can be obtained by a method based on Production Method 1 or Step 2 of Production Method 2.

The conversion of a functional group contained in $R^1$ or $R^2$ in Compound (I) can also be carried out by a known method [for example, a method described in Comprehensive Organic Transformations 2nd edition, written by R. C. Larock, Vch Verlagsgesellschaft Mbh (1999), and the like] or a modified method thereof.

The intermediates and the target compounds in the above-described respective production methods can be isolated and purified by applying separation and purification methods commonly used in the synthetic organic chemistry such as filtration, extraction, washing, drying, concentration, recrystallization, various types of chromatography, and the like. Further, the intermediates can also be subjected to a next reaction without particularly purification.

Among Compounds (I), some compounds may exist as a stereoisomer such as a geometric isomer, an optical isomer, and the like, a tautomer, and the like. The present invention encompasses all possible isomers and mixtures thereof including them.

A part or all of the respective atoms in Compound (I) may be replaced by corresponding isotope atom(s), respectively, and the present invention also encompasses such compounds replaced by isotope atom(s). For example, a part or all of the hydrogen atoms in Compound (I) may be a hydrogen atom having an atomic weight of 2 (deuterium atom).

A compound in which a part or all of the respective atoms in Compound (I) is/are replaced by corresponding isotope atom(s), respectively, can be produced in the same manner as in each of the above-described production methods using a commercially available building block. In addition, the compound in which a part or all of the hydrogen atoms in Compound (I) is/are replaced by deuterium atom(s) can also be synthesized by, for example, 1) a method using deuterium peroxide to deuterate carboxylic acid and the like under basic conditions (U.S. Pat. No. 3,849,458), 2) a method using an iridium complex as a catalyst and also using heavy water as a deuterium source to deuterate alcohol, carboxylic acid, and the like [J. Am. Chem. Soc. Vol. 124, No. 10, 2092 (2002)], 3) a method using palladium carbon as a catalyst and also using only a deuterium gas as a deuterium source to deuterate fatty acid [LIPIDS, Vol. 9, No. 11, 913 (1974)], 4) a method using a metal such as platinum, palladium, rhodium, ruthenium, and iridium as a catalyst and also using heavy water, or heavy water and a deuterium gas, as a deuterium source to deuterate acrylic acid, methyl acrylate, methacrylic acid, methyl methacrylate, and the like (JPH5-19536, JPS61-277648, and JPS61-275241), 5) a method using a catalyst such as palladium, nickel, copper, and chromite copper and also using heavy water as a deuterium source to deuterate acrylic acid, methyl methacrylate, and the like (JPS63-198638), and the like.

The present invention also includes a prodrug of Compound (I). The prodrug of Compound (I) is a compound which is converted to Compound (I) by a reaction with an enzyme, gastric acid, and the like in the body. As the prodrug, many types thereof are known, and a suitable prodrug can be selected based on a known literature (see, for example, Iyakuhin no Kaihatsu (Development of Pharmaceuticals), Hirokawa Shoten, 1990, vol. 7, p. 163) and synthesized by a known method. For example, as a prodrug of Compound (I), when Compound (I) has amino, a compound in which the amino is acylated, alkylated, or phosphorylated, when Compound (I) has hydroxy, a compound in which the hydroxy is acylated, alkylated, phosphorylated, or borated, when Compound (I) has carboxy, a compound in which the carboxy is esterified or amidated, and the like can be exemplified. Further, the prodrug of Compound (I) may be any of a hydrate, a non-hydrate, and a solvate, and may form a salt with a pharmaceutically acceptable acid or base in the same manner as in the case of Compound (I).

In the case where a salt of Compound (I) is to be obtained, when Compound (I) is obtained in the form of a salt, the salt may be directly purified. When Compound (I) is obtained in a free form, Compound (I) is dissolved or suspended in a suitable solvent, and an acid or a base is added thereto to form a salt, and then, the salt may be isolated and purified.

Further, Compound (I) and a pharmaceutically acceptable salt thereof may exist in the form of an adduct with water or any of various solvents, and the present invention also encompasses such an adduct.

Specific examples of Compound (I) obtained by the present invention are shown in Table 1 to Table 4. However, the compounds of the present invention are not limited thereto. Incidentally, Compound 3 and Compound 4 in Table 1 have a diastereomeric relationship with each other.

[Table 1]

TABLE 1

| Compound No. | $R^1$— | —$R^2$ |
|---|---|---|
| 1 | HO₂C-[tetrahydrofuranone ring with HO₂C substituent] | OH |
| 2 | HO | OH |

TABLE 1-continued

[Structure shown: R¹-C(=O)-CH(CH₃)-CH₂-C(=CH-C(CH₃)=CH-CH(CH₃)-CH₂-CH(CH₃)-CH₂-CH(CH₃)-CH₂-CH(CH₃)-CH₂-CH₃)-C(=O)-R²]

| Compound No. | R¹— | —R² |
|---|---|---|
| 3 | NaO₂C–CH(OH)–CH(CO₂Na)–CH(CO₂Na)–O– | –ONa |
| 4 | NaO₂C–CH(OH)–CH(CO₂Na)–CH(CO₂Na)–O– | –ONa |
| 5 | (furanone with CO₂CH₃ groups)–O– | –OCH₃ |
| 6 | H₃C-O-C(=O)–CH(OH)–CH(CH(OH)OCH₃)–CH(CO₂H)–O– | –OCH₃ |
| 7 | H₃C-O-C(=O)–CH(OH)–CH(CH(OCH₃)C(=O)OCH₃)–CH(CO₂CH₃)–O– | –OCH₃ |
| 8 | HO– | –O–C(CH₃)₃ |
| 9 | HO₂C–CH₂–O– | –OH |
| 10 | H₃C–O– | –OH |
| 11 | HO₂C–CH₂–CH₂–O– | –OH |
| 12 | HO₂C–CH₂–CH₂–CH₂–O– | –OH |
| 13 | HO–CH₂–CH₂–CH₂–O– | –OH |
| 14 | HO₂C–CH₂–CH(CO₂H)–O– | –OH |

[Table 2]

TABLE 2

[Structure shown: R¹-C(=O)-CH(CH₃)-CH₂-C(=CH-C(CH₃)=CH-CH(CH₃)-CH₂-CH(CH₃)-CH₂-CH(CH₃)-CH₂-CH(CH₃)-CH₂-CH₃)-C(=O)-R²]

| Compound No. | R¹— | —R² |
|---|---|---|
| 15 | (γ-butyrolactone with O-substituent) | –OH |
| 16 | HO–CH(CO₂H)–CH₂–CH₂–O– | –OH |
| 17 | (EtO)₂P(=O)–O–CH(CO₂H)–CH(CO₂H)–O– | –OH |
| 18 | HO₂C–CH₂–CH(CO₂H)–O– | –OH |
| 19 | HO–CH₂–CH(OH)–CH₂–O– | –OH |
| 20 | (γ-butyrolactone with O-substituent) | –OH |
| 21 | (γ-butyrolactone with O-substituent) | –OH |
| 22 | HO₂C–CH(CO₂H)–O– | –OH |
| 23 | HO₂C–CH₂–CH(CO₂H)–CH(CO₂H)–O– | –OH |
| 24 | HO₂C–CH₂–CH(CO₂H)–CH₂–O– | –OH |
| 25 | HO₂C–CH(NH–CH₂–CO₂H)–CH₂–O– | –OH |

TABLE 2-continued
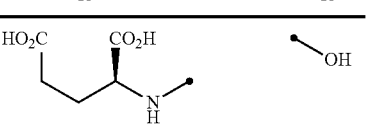
| Compound No. | R¹— | —R² |
|---|---|---|
| 26 | 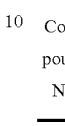 | 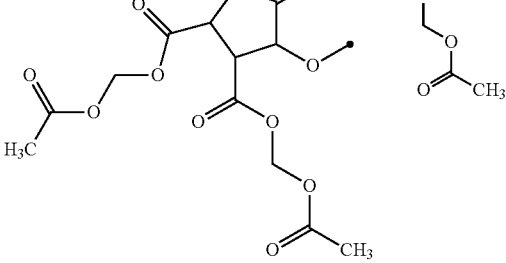 |
[Table 3]
TABLE 3
| Compound No. | R¹— | —R² |
|---|---|---|
| 27 | 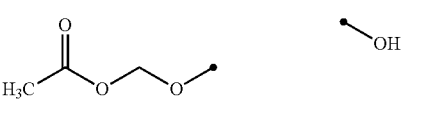 |  |
TABLE 3-continued
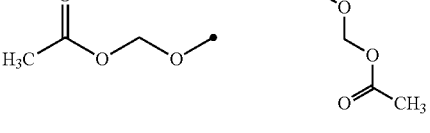
| Compound No. | R¹— | —R² |
|---|---|---|
| 28 |  | 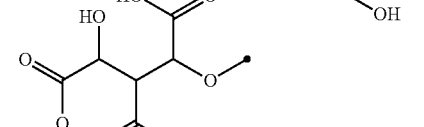 |
| 29 |  | 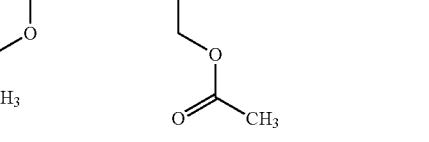 |
| 30 |  | 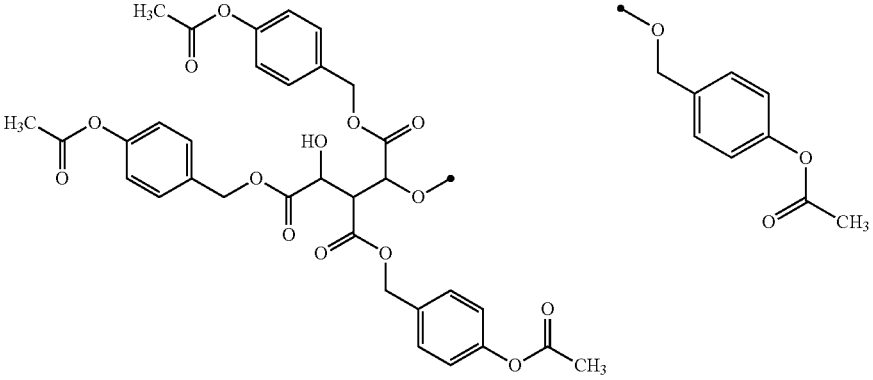 |
[Table 4]
TABLE 4
| Compound No. | R¹— | —R² |
|---|---|---|
| 31 | | |

TABLE 4-continued

[Structure: R¹—C(=O)—CH(CH₃)—CH₂—C(=CH—CH=C(CH₃)—CH(CH₃)—CH(CH₃)—CH(CH₃)—CH(CH₃)—CH₂CH₃)—C(=O)—R²]

| Compound No. | R¹— | —R² |
|---|---|---|
| 32 | [tetrahydrofuran-2-one-4-yl-oxy group] | —O—CH₃ |

Next, the pharmacological effect of representative Compound (I) is specifically explained by Test Examples.

Test Example 1

Cell Growth Inhibition Test Against Human Cervical Cancer Cells

As a cervical cancer cell line, a human cervical cancer cell line HeLa (DS Pharma Biomedical, Cat. No. EC93021013-F0) was used.

For the culture of the cell line, MEM Earle's (Gibco Invitrogen, Cat. No. 11095-080) containing 10 vol % Fetal Bovine Serum (FBS) (Gibco Invitrogen, Cat. No. 10091-148), a 1 vol % MEM Non-Essential Amino Acids Solution (10 mmol/L) (Gibco Invitrogen, Cat. No. 11140-050), and a 1 vol % Penicillin-Streptomycin liquid (Gibco Invitrogen, Cat. No, 15140-122) was used. The cell line was cultured under conditions of 37° C. and 5% carbon dioxide.

The HeLa cells ($1.33 \times 10^4$ cells/mL) suspended in a cell culture medium not containing Penicillin-Streptomycin (MEM containing 10 vol % FBS and a 1 vol % MEM Non-Essential Amino Acids Solution (10 mmol/L)) were inoculated in a flat-bottomed 96-well plate (Nunc, Cat. No. 167008) at 60 μL/well ($8 \times 10^2$ cells/well) and cultured under conditions of 37° C. and 5% carbon dioxide for 24 hours. Then, a test compound solution serially diluted with OPTI-MEM I Reduced Serum Medium (Invitrogen, Cat. No. 31985-070) was added thereto at 40 μL/well, and the cells were further cultured for 72 hours.

A viable cell count reagent SF (Nacalai Tesque, Cat. No. 07553-44) was added to each well at 10 μL/well, and the plate was incubated under conditions of 37° C. and 5% carbon dioxide for 3 hours. Then, by using a microplate reader (Spectramax 340PC[384], Molecular Devices), a difference in absorbance between 460 nm and 650 nm in each well was measured.

The difference in absorbance in the well in which the cells were not treated with the compound was taken as 100%, and the difference in absorbance in the well in which the cells were not inoculated was taken as 0%, and the cell growth ratio (%) was calculated based on the difference in absorbance in the compound-treated group.

Compounds 1 to 30 and 32 inhibited the cell growth of the human cervical cancer cell line HeLa by 90% or more when the concentration of the compound was 200 μmol/L. Further, Compounds 1, 3, and 27 inhibited the cell growth by 90% or more when the concentration of the compound was 20 μmol/L.

Based on these results, it was found that Compound (I) has a cell growth inhibitory activity against the human cervical cancer cells. That is, it is considered that Compound (I) is useful as an anti-tumor agent.

Compound (I) or a pharmaceutically acceptable salt thereof can be administered alone. However, usually, Compound (I) or a pharmaceutically acceptable salt thereof is preferably provided in various pharmaceutical preparations. In addition, such pharmaceutical preparations are used for animals and humans.

The pharmaceutical preparation according to the present invention can contain, as an active ingredient, Compound (I) or a pharmaceutically acceptable salt thereof alone or as a mixture with any other active ingredient for other treatment. Further, such pharmaceutical preparations are prepared by mixing the active ingredient with one or more pharmaceutically acceptable carriers and then subjecting the mixture to any method well known in the technical field of pharmaceutics.

As for the administration route, it is preferred to select the most effective route of administration in the treatment. Examples of the administration route include oral administration and parenteral administration such as intravenous administration.

Examples of the dosage form include a tablet, an injection, and the like.

A suitable dosage form for the oral administration, for example, a tablet and the like can be prepared by using an excipient such as lactose, a disintegrator such as starch, a lubricant such as magnesium stearate, a binder such as hydroxypropylcellulose, and the like.

A suitable dosage form for the parenteral administration, for example, an injection can be prepared by using a salt solution, a glucose solution, or a mixture of a salt solution and a glucose solution, or the like.

The dose and the frequency of administration of Compound (I) or a pharmaceutically acceptable salt thereof may vary depending on dosage form, age and body weight of a patient, nature or seriousness of the symptom to be treated, and the like. However, in the oral administration, in general, a dose of 0.01 mg to 1 g, preferably, 0.05 to 100 mg, is administered to an adult person once or several times a day. In the parenteral administration such as intravenous administration, a dose of 0.001 to 100 mg, preferably, 0.01 to 10 mg, is administered to an adult person once or several times a day. However, such dose and frequency of administration vary depending on the above-described various conditions.

Hereinafter, the present invention will be more specifically described by Examples, however, the scope of the present invention is not limited to these Examples.

Incidentally, the proton nuclear magnetic resonance spectrum ($^1$H NMR) used in the Examples was measured at 500 MHz, and exchangeable protons may not be clearly observed depending on the compound and measurement conditions. Incidentally, the multiplicity of signals is expressed in conventional terms, and the term br indicates an apparently broad signal.

Example 1

4-{(4Z,6E)-4-Carboxy-2,6,8,10,12,14-hexamethyl-hexadec-4,6-dienoyloxy}-5-oxotetrahydrofuran-2,3-dicarboxylic Acid (Compound 1)

(Z)-2-Methyl-4-{(E)-2,4,6,8,10-pentamethyldodec-2-enylidene}pentanedicarboxylic Acid (Compound 2)

As a strain, a *Scopulariopsis* sp. CPM1007 strain (NITE BP-1377) was used. One piece of agar containing the strain was inoculated in a first seed medium (10 mL) placed in a 70-mL test tube, and the strain was shaking-cultured at 28° C. for 96 hours. Subsequently, the first seed medium (5 mL) was inoculated in a second seed medium (45 mL) placed in a 300-mL Erlenmeyer flask, and the strain was shaking-cultured at 28° C. for 48 hours. Subsequently, the second seed medium (50 mL) was inoculated in a third seed medium (450 mL) placed in a 2-L Erlenmeyer flask, and the strain was shaking-cultured at 28° C. for 43 hours. As the first to third seed media, a medium (pH 6.5) having a composition containing glucose (20 g/L), mashed potato (30 g/L), and dry yeast extract (5 g/L) was used. Subsequently, as the main fermentation medium, a medium obtained by placing oatmeal (70 g), soybean powder (7 g), and water (140 mL) in a polypropylene container, followed by sterilization was used, and 40 containers containing the medium were prepared, and the third seed culture broth (24 mL) was inoculated in each container, and the strain was stationary-cultured at 25° C. for 12 days.

The thus obtained fermentation culture, (about 6 kg) was extracted at room temperature with isopropanol (8.2 L), and then extracted with isopropanol/water (a 1:1 mixed solution) (7.0 L), and then extracted with isopropanol/water (a 1:1 mixed solution) (6.9 L). The obtained extract was diluted with water and purified by Diaion (registered trademark) HP-20 (Mitsubishi Chemical Corporation) column chromatography (acetone containing 0.1% trifluoroacetic acid (TFA)/water containing 0.1% TFA). A fraction eluted with 75% acetone containing 0.1% TFA was concentrated under reduced pressure, and the resulting residue was extracted with ethyl acetate, whereby an extract (13.0 g) was obtained. The total amount of the extract was purified by Cosmosil 140 C18-OPN (Nacalai Tesque, Cat. No. 37878-45) column chromatography (acetonitrile containing 0.1% TFA/water containing 0.1% TFA). A fraction (4 L) eluted with 70% and 80% acetonitrile containing 0.1% TFA was concentrated under reduced pressure, and the resulting residue was extracted with ethyl acetate, whereby an extract (5.91 g) was obtained. The total amount of the extract was purified by high performance liquid chromatography (column: Waters SunFire (registered trademark) C18, 19×250 mm, Cat. No. 186002669, mobile phase: acetonitrile containing 0.1% TFA/water containing 0.1% TFA), whereby Compound 1 (1.92 g) and Compound 2 (636.1 rag) were obtained respectively.

Compound 1: $^1$H NMR (acetone-$d_6$) δ6.19 (1H, s), 5.90 (1H, d, J=8.7 Hz), 5.36 (1H, d, J=9.5 Hz), 5.25 (1H, d, J=8.7 Hz), 3.75 (1H, t, J=8.7 Hz), 2.80 (1H, m), 2.76 (1H, m), 2.57 (1H, m), 2.30 (1H, m), 1.80 (3H, s), 1.59 (1H, m), 1.58 (1H, m), 1.45 (1H, m), 1.37 (1H, m), 1.25 (2H, m), 1.23 (1H, m), 1.20 (3H, d, J=6.9 Hz), 1.06 (1H, m), 1.03 (1H, m), 0.92 (3H, d, J=6.6 Hz), 0.91 (1H, m), 0.89 (1H, m), 0.88 (3H, d, J 6.6 Hz), 0.86 (3H, d, J=6.5 Hz), 0.853 (3H, t; J=7.5 Hz), 0.850 (3H, d, J=6.6 Hz).

Compound 2: $^1$H NMR (CDCl$_3$) δ6.10 (1H, s), 5.33 (1H, d, J=9.4 Hz), 2.67-2.41 (4H, m), 1.77 (3H, s), 1.60-1.45 (2H, m), 1.44-1.31 (2H, m), 1.27-1.13 (3H, m), 1.18 (3H, d, J=6.2 Hz), 1.08-0.92 (2H, m), 0.90 (3H, d, J=6.6 Hz), 0.86-0.81 (14H, m).

Example 2

1-{(4Z,6E)-4-Carboxy-2,6,8,10,12,14-hexamethyl-hexadec-4,6-dienoyloxy}-3-hydroxypropane-1,2,3-tricarboxylic Acid 4-sodium Salt (Compound 3)

To Compound 1 (2.54 g, 4.45 mmol), THF (139 mL), sodium hydrogen carbonate (7.48 g, 89 mmol), and water (139 mL) were added, and the resulting mixture was stirred at room temperature for 18 hours. The reaction mixture was purified by Diaion (registered trademark) HP-20 (Mitsubishi Chemical Corporation) column chromatography (water/methanol), whereby Compound 3 (1.95 g, 67%) was obtained.

$^1$H-NMR (D$_2$O) δ5.81 (1H, d, J=1.0 Hz), 5.44 (1H, d, J=10.0 Hz), 5.16 (1H, d, J=5.9 Hz), 4.35 (1H, d, J=6.2 Hz), 3.23 (1H, t, J=5.9 Hz), 2.83 (1H, dd, J=14.2, 4.3 Hz), 2.77-2.69 (1H, m), 2.68-2.57 (1H, m), 2.20 (1H, dd, J=14.2, 9.9 Hz), 1.86 (3H, s), 1.67-1.54 (2H, m), 1.53-1.45 (1H, m), 1.45-1.20 (5H, m), 1.23 (3H, d, J=7.0 Hz), 1.17-1.06 (2H, m), 0.97 (3H, d, J=6.8 Hz), 0.92 (3H, d, J=6.8 Hz), 0.98-0.35 (11H, m).

Example 3

1-{(4Z,6E)-4-Carboxy-2,6,8,10,12,14-hexamethyl-hexadec-4,6-dienoyloxy}-3-hydroxypropane-1,2,3-tricarboxylic Acid 4-sodium Salt (Compound 4)

(Step 1) To Compound 1 (1.33 g, 2.41 mmol), THF (20 mL), water (20 mL), and sodium carbonate (1.02 g, 9.62 mmol) were added, and the resulting mixture was stirred at room temperature for 30 minutes. The solvent in the reaction mixture was evaporated under reduced pressure. The resulting residue was purified by Diaion (registered trademark) HP-20ss (Mitsubishi Chemical Corporation) column chromatography (water/methanol), and to the residue, water (20 mL) and Dowex 50 (registered trademark) (Muromachi Technos, 50WX8, 50-100 mesh, H$^+$ form) (10 g) were added, and the resulting mixture was gently stirred at room temperature for 30 minutes. The reaction mixture was filtered, and the filtrate was extracted with ethyl acetate. The organic layer was dried over anhydrous sodium sulfate, and the solvent was evaporated under reduced pressure. The resulting residue was purified by high performance liquid chromatography (column: Waters SunFire (registered trademark) C18, 19×250 mm, Cat. No. 186002669; mobile phase: acetonitrile containing 0.1% TFA/water containing 0.1% TFA), whereby 1-{(4Z,6E)-4-carboxy-2,6,8,10,12,14-hexamethylhexadec-4,6-dienoyloxy}-3-hydroxypropane-1,2,3-tricarboxylic acid (174 mg) was obtained.

(Step 2) To 1-{(4Z,6E)-4-carboxy-2,6,8,10,12,14-hexamethylhexadec-4,6-dienoyloxy}-3-hydroxypropane-1,2,3-tricarboxylic acid (174 mg, 0.306 mmol) obtained in Step 1, THF (5 mL), water (5 mL), and sodium carbonate (140 mg, 1.32 mmol) were added, and the resulting mixture was stirred at room temperature for 30 minutes. The solvent in the reaction mixture was evaporated under reduced pressure. The resulting residue was purified by Diaion (registered trademark) HP-20ss column chromatography (water/methanol), whereby Compound 4 (119.6 mg, 59%) was obtained.

$^1$H NMR (D$_2$O) δ5.77 (1H, s), 5.40 (1H, d, J=9.3 Hz), 5.11 (1H, d, J=8.7 Hz), 4.16 (1H, d, J=2.2 Hz), 3.22 (1H, dd, J=8.7, 2.2 Hz), 2.81-2.67 (2H, m), 2.60 (m), 2.20 (1H, m), 1.83 (3H, s), 1.63-1.51 (2H, m), 1.46 (1H, m), 1.37 (1H, m), 1.32-1.18 (3H, m), 1.22 (3H, d, J=6.8 Hz), 1.14-1.00 (2H, m), 0.89 (3H, d, J=6.6 Hz), 0.87-0.84 (14H, m).

Example 4

Dimethyl 4-{(4Z,6E)-4-(methoxycarbonyl)-2,6,8,10,12,14-hexamethylhexadec-4,6-dienoyloxy}-5-oxotetrahydrofuran-2,3-dicarboxylate (Compound 5)

4-Hydroxy-5-methoxy-3-(methoxycarbonyl)-2-{(4Z,6E)-4-(methoxycarbonyl)-2,6,8,10,12,14-hexamethylhexadec-4,6-dienoyloxy}-5-oxopentanoic Acid (Compound 6)

To Compound 1 (200 mg, 0.362 mmol), methanol (6 mL) and a 0.6 mol/L trimethylsilyldiazomethane/n-hexane solution (4 ml, 2.4 mmol) were added, and the resulting mixture was stirred at 0° C. for 20 minutes. The temperature of the reaction mixture was raised to room temperature, and the solvent was evaporated under reduced pressure. The resulting residue was purified by silica gel column chromatography (n-hexane/ethyl acetate), whereby Compound 5 (124.7 mg, 58%) and Compound 6 (54.8 mg, 25%) were obtained, respectively.

Compound 5: $^1$H NMR (CDCl$_3$) δ6.12 (1H, s), 5.62 (1H, d, J=8.7 Hz), 5.26 (1H, d, J=8.4 Hz), 5.08 (1H, d, J=8.7 Hz), 3.85 (3H, s), 3.80 (3H, s), 3.69 (3H, s), 3.54 (1H, t, J=8.7 Hz), 2.75 (1H, m), 2.68 (1H, dd, J=14.6, 7.0 Hz), 2.47 (1H, m), 2.33 (1H, dd, J=14.6, 7.6 Hz), 1.68 (3H, d, J=1.1 Hz), 1.59-1.47 (2H, m), 1.43-1.29 (2H, m), 1.20 (3H, d, J=6.9 Hz), 1.23-1.13 (3H, m), 1.06-0.92 (2H, m), 0.89 (3H, d, J=6.6 Hz), 0.87-0.81 (14H, m).

Compound 6: $^1$H NMR (CDCl$_3$) δ6.11 (1H, s), 5.58 (1H, d, J=3.7 Hz), 5.28 (1H, d, J=9.5 Hz), 4.66 (1H, d, J=7.7 Hz), 3.79 (3H, s), 3.72 (3H, s), 3.71 (3H, s), 3.59 (1H, dd, J=7.7, 3.7 Hz), 2.71-2.60 (2H, m), 2.48 (1H, m), 2.41 (1H, m, J=13.1, 5.2 Hz), 1.68 (3H, d, J=6.9 Hz), 1.59-1.46 (2H, m), 1.45-1.30 (2H, m), 1.21 (3H, d, J=6.9 Hz), 1.23-1.13 (3H, m), 1.08-0.93 (2H, m), 0.90 (3H, d, J=6.6 Hz), 0.88-0.82 (14H, m).

Example 5

Trimethyl 1-hydroxy-3-{(4Z,6E)-4(methoxycarbonyl)-2,6,8,10,12,14-hexamethylhexadec-4,6-dienoyloxy}-propane-1,2,3-tricarboxylate (Compound 7)

To 1-{(4Z,6E)-4-carboxy-2,6,8,10,12,14-hexamethylhexadec-4,6-dienoyloxy}-3-hydroxypropane-1,2,3-tricarboxylic acid (33.1 mg, 0.0581 mmol) obtained in the same manner as Step 1 of Example 3, methanol (3 mL) was added, and the resulting mixture was cooled to 0° C., and then, a 0.6 mol/L trimethylsilyldiazomethane/n-hexane solution (2 mL, 1.2 mmol) was added thereto, and the resulting mixture was stirred at room temperature for 30 minutes. The solvent in the reaction mixture was evaporated under reduced pressure. The resulting residue was purified by silica gel preparative thin-layer chromatography (n-hexane/ethyl acetate), whereby Compound 7 (20.0 mg, 55%) was obtained.

$^1$H NMR (CDCl$_3$) δ6.10 (1H, s), 5.63 (1H, d, J=7.6 Hz), 5.26 (1H, d, J=9.4 Hz), 4.55 (1H, dd, J=6.3, 3.3 Hz), 3.81 (3H, s), 3.75 (3H, s), 3.71 (3H, s), 3.69 (3H, s), 3.62 (1H, dd, J=7.6, 3.3 Hz), 3.38 (1H, d, J=6.3 Hz), 2.74-2.66 (2H, m), 2.47 (1H, m), 2.31 (1H, m), 1.67 (3H, d, J=1.1 Hz), 1.58-1.46 (2H, m), 1.45-1.31 (2H, m), 1.28-1.13 (3H, m), 1.21 (3H, d, J=6.9 Hz), 1.07-0.94 (2H, m), 0.89 (3H, d, J=6.6 Hz), 0.92-0.81 (14H, m).

Example 6

(4Z,6E)-4-(tert-Butoxycarbonyl)-2,6,8,10,12,14-hexamethylhexadec-4,6-dienoic Acid (Compound 8)

(Step 1) To N,N'-diisopropylcarbodiimide (6.16 mL, 39.5 mmol), tert-batanol (3.95 mL, 41.3 mmol) and copper(I) chloride (238 mg, 2.41 mmol) were added, and the resulting mixture was stirred at room temperature for 24 hours. The reaction mixture was filtered through Celite (registered trademark), and the solvent in the filtrate was evaporated under reduced pressure. To the residue, dichloromethane (49 mL) and Compound 1 (1.90 g, 3.44 mmol) were added, and the resulting mixture was stirred for 22 hours. The reaction mixture was filtered through Celite (registered trademark), and to the filtrate, water was added, and the resulting mixture was extracted with chloroform. The organic layer was washed with saturated brine and dried over sodium sulfate, and then, the solvent was evaporated under reduced pressure. The resulting residue was purified by silica gel column chromatography (ethyl acetate/n-hexane=0/100 to 10/90), whereby di-tert-butyl 4-{(4Z,6E)-4-(tert-butoxycarbonyl)-2,6,8,10,12,14-hexamethylhexadec-4,6-dienoyloxy}-5-oxotetrahydrofuran-2,3-dicarboxylate (606 mg, 24%) was obtained.

$^1$H-NMR (CDCl$_5$) 6.00 (1H, s), 5.69 (1H, d, J=9.5 Hz), 5.30 (1H, d, J=9.5 Hz), 4.93 (1H, d, J=9.1 Hz), 3.31 (1H, dd, J=9.3, 9.3 Hz), 2.75 (2H, td, J=11.2, 5.0 Hz), 2.54-2.44 (1H, m), 2.22 (1H, td, J=11.1, 4.9 Hz), 1.76 (3H, s), 1.55 (9H, s), 1.49 (9H, s), 1.48 (9H, s), 1.64-1.43 (2H, m), 1.43-1.28 (2H, m), 1.22 (3H, d, J=6.5 Hz), 1.24-1.11 (3H, m), 1.08-0.95 (2H, m), 0.92 (3H, d, J=6.8 Hz), 0.94-0.80 (14H, m).

(Step 2) To di-tert-butyl 4-{(4Z,6E)-4-(tert-butoxycarbonyl)-2,6,8,10,12,14-hexamethylhexadec-4,6-dienoyloxy}-5-oxotetrahydrofuran-2,3-dicarboxylate (500 mg, 0.694 mmol) obtained in Step 1, acetonitrile (35 mL) and an aqueous sodium hydroxide solution (0.25 mol/L, 28 mL, 6.94 mmol) were added, and the resulting mixture was stirred at room temperature for 6.5 hours. To the reaction mixture, water was added, and then, Dowex 50 (registered trademark) (Muromachi Technos, 50WX8, 50-100 mesh, H$^+$ form) was added thereto to neutralize the mixture, and the insoluble matter was removed by filtration. After the filtrate was extracted with ethyl acetate, the organic layer was washed with saturated brine and dried over sodium sulfate, and then, the solvent was evaporated under reduced pressure. The resulting residue was purified by silica gel column chromatography (ethyl acetate/n-hexane=5/95 to 60/40), whereby Compound 8 (318 mg, quant.) was obtained.

$^1$H-NMR (CDCl$_3$) δ5.98 (1H, s), 5.29 (1H, d, J=9.1 Hz), 2.72-2.64 (2H, m), 2.55-2.45 (1H, m), 2.26 (1H, dd, J=16.0, 10.3 Hz), 1.76 (3H, s), 1.51 (9H, s), 1.65-1.45 (1H, m), 1.45-1.30 (3H, m), 1.21 (3H, d, J=7.5 Hz), 1.30-1.12 (3H, m), 1.08-0.96 (2H, m), 0.92 (3H, d, J=7.0 Hz), 0.94-0.80 (14H, m).

Example 7

(2Z,4E)-2-{3-(Carboxymethoxy)-2-methyl-3-oxopropyl}-4,6,8,10,12-pentamethyltetradec-2,4-dienoic Acid (Compound 9)

(Step 1) To Compound 8 (16 mg, 0.037 mmol), dichloromethane (1.8 mL), tert-butyl 2-hydroxyacetate (5.8 mg, 0.044 mmol), EDC.HCl (10.5 mg, 0.055 mmol), and DMAP (0.4 mg, 0.0037 mmol) were added, and the resulting mixture was stirred at room temperature for 4 days. The solvent was evaporated under reduced pressure, and the resulting residue was purified by thin-layer column chromatography (ethyl acetate/n-hexane=1/9), whereby 1-(2-tert-butoxy-2-oxoethyl) 5-tert-butyl (Z)-2-methyl-4-{(E)-2,4,6,8,10-pentamethyldodec-2-enylidene}pentanedioate (14.7 mg, 73%) was obtained.

$^1$H-NMR (CDCl$_3$) δ5.97 (1H, s), 5.28 (1H, d, J=9.4 Hz), 4.54 (1H, d, J=15.5 Hz), 4.43 (1H, d, J=15.5 Hz), 2.79-2.69 (2H, m), 2.54-2.44 (1H, m), 2.24 (1H, dd, J=13.3, 7.5 Hz), 1.75 (3H, s), 1.49 (9H, s), 1.47 (9H, s), 1.64-1.31 (4H, m), 1.22 (3H, dd, J=6.9 Hz), 1.27-1.12 (3H, m), 1.09-0.96 (2H, m), 0.91 (3H, d, J=6.7 Hz), 0.93-0.79 (14H, m).

(Step 2) To 1-(2-tert-butoxy-2-oxoethyl) 5-tert-butyl (Z)-2-methyl-4-{(E)-2,4,6,8,10-pentamethyldodec-2-enylidene}pentanedioate (14.7 mg, 0.027 mmol) obtained in Step 1, dichloromethane (2 mL) and trifluoroacetic acid (0.2 mL, 2.6 mmol) were added, and the resulting mixture was stirred at room temperature for 24 hours. The solvent was evaporated under reduced pressure, and the resulting residue was purified by thin-layer column chromatography (methanol/chloroform=1/9), whereby Compound 9 (8.6 mg, 74%) was obtained.

$^1$H-NMR (CDCl$_3$) δ6.14 (1H, s), 5.71 (2H, br s), 5.32 (1H, d, J=10.0 Hz), 4.65 (1H, d, J=15.6 Hz), 4.53 (1H, d, J=15.6 Hz), 2.84-2.75 (1H, m), 2.75-2.65 (1H, m), 2.54-2.44 (1H, m), 2.39 (1H, dd, J=13.3, 5.7 Hz), 1.75 (3H, s), 1.59-1.46 (2H, m), 1.45-1.30 (2H, m), 1.30-1.10 (4H, m), 1.20 (3H, d, J=7.0 Hz), 1.09-0.93 (1H, m), 0.90 (3H, d, J=6.7 Hz), 0.90-0.30 (14H, m).

Example 8

(2Z,4E)-2-(3-Methoxy-2-methyl-3-oxopropyl)-4,6,8,10,12-pentamethyltetradec-2,4-dienoic Acid (Compound 10)

(Step 1) In the same manner as Step 1 of Example 7, 1-tert-butyl 5-{(3aR,4R,6aR)-2,2-dimethyl-6-oxotetrahydrofuro[3,4-d][1,3]dioxol-4-yl}methyl (Z)-4-methyl-2-{(E)-2,4,6,8,10-pentamethyldodec-2-enylidene}pentanedioate (29.6 mg, 71%) was obtained by using Compound 8 (30 mg, 0.069 mmol) and (3aR,6R,6aR)-6-(hydroxymethyl)-2,2-dimethyldihydroxyfuro[3,4-d][1,3]dioxol-4(3aH)-one (15.5 mg, 0.082 mmol).

$^1$H-NMR (CDCl$_3$) δ5.91 (1H, s), 5.35-5.23 (1H, m), 4.92-4.82 (2H, m), 4.78-4.66 (2H, m), 4.33-4.24 (1H, m), 4.24-4.14 (1H, m), 2.76-2.40 (3H, m), 2.34-2.24 (1H, m), 1.73 (3H, s), 1.58-1.09 (22H, m), 1.15 (3H, d, J=6.6 Hz), 1.08-0.94 (2H, m), 0.90 (3H, d, J=6.6 Hz), 0.92-0.78 (14H, m)

(Step 2) To 1-tert-butyl 5-{(3aR,4R,6aR)-2,2-dimethyl-6-oxotetranydrofuro[3,4-d][1,3]dioxol-4-yl}methyl (Z)-4-methyl-2-{(E)-2,4,6,8,10-pentamethyldodec-2-enylidene}pentanedioate (29 mg, 0.048 mmol) obtained in Step 1, methanol (2 mL) and a 10% hydrochloric acid-methanol solution (0.2 mL, 0.43 mmol) were added, and the resulting mixture was stirred at room temperature for 3 days. The solvent was evaporated under reduced pressure, and the resulting residue was purified by thin-layer column chromatography (ethyl acetate/n-hexane=1/3), whereby Compound 10 (2.8 mg, 15%) was obtained.

$^1$H-NMR (CDCl$_3$) δ6.21 (1H, s), 5.33 (1H, d, J=9.5 Hz), 3.67 (3H, s), 2.79-2.71 (1H, m), 2.62 (1H, dd, J=13.7, 7.8 Hz), 2.55-2.46 (1H, m), 2.39 (1H, dd, J=13.7, 7.3 Hz), 1.77 (3H, d, J=1.2 Hz), 1.59-1.47 (2H, m), 1.44-1.31 (2H, m), 1.29-1.13 (3H, m), 1.19 (3H, d, J=7.0 Hz), 1.09-0.95 (2H, m), 0.91 (3H, d, J=6.6 Hz), 0.93-0.81 (14H, m).

Example 9

(2Z,4E)-2-{3-(2-Carboxyethoxy)-2-methyl-3-oxopropyl}-4,6,8,10,12-pentamethyltetradec-2,4-dienoic Acid (Compound 11)

(Step 1) In the same manner as Step 1 of Example 7, 1-(3-tert-butoxy-3-oxopropyl) 5-tert-butyl (2)-2-methyl-4-{(E)-2,4,6,8,10-pentamethyldodec-2-enylidene}pentanedioate (20 mg, 77%) was obtained by using Compound 8 (20 mg, 0.044 mmol) and tert-butyl 3-hydroxypropionate (0.0081 mL, 0.055 mmol).

$^1$H-NMR (CDCl$_3$) δ5.95 (1H, s), 5.28 (1H, d, J=9.3 Hz), 4.35-4.25 (2H, m), 2.70-2.57 (2H, m), 2.54 (2H, dd, J=6.6, 6.6 Hz), 2.53-2.44 (1H, m), 2.20 (1H, dd, J=13.3, 7.9 Hz), 1.75 (3H, s), 1.50 (9H, s), 1.45 (9H, s), 1.59-1.30 (4H, m), 1.27-1.12 (3H, m), 1.15 (3H, d, J=6.9 Hz), 1.10-0.93 (2H, m), 0.91 (3H, d, J=6.6 Hz), 0.93-0.80 (14H, m).

(Step 2) In the same manner as Step 2 of Example 7, Compound 11 (13.3 mg, 83%) was obtained by using 1-(3-tert-butoxy-3-oxopropyl) 5-tert-butyl (Z)-2-methyl-4-{(E)-2,4,6,8,10-pentamethyldodec-2-enylidene}pentanedioate (20 mg, 0.035 mmol) obtained in Step 1.

$^1$H-NMR (CDCl$_3$) δ9.17 (2H, br s), 6.20 (1H, s), 5.33 (1H, dd, J=9.7 Hz), 4.46-4.39 (1H, m), 4.30-4.23 (1H, m), 2.73 (1H, ddd, J=7.2, 7.2, 7.2 Hz), 2.70-2.54 (2H, m), 2.54-2.44 (1H, m), 2.39 (1H, dd, J=13.9, 6.9 Hz), 1.76 (3H, s), 1.60-1.46 (2H, m), 1.45-1.29 (2H, m), 1.29-1.11 (4H, m), 1.17 (3H, d, J=7.2 Hz), 1.09-0.93 (2H, m), 0.90 (3H, d, J=6.6 Hz), 0.93-0.79 (14H, m).

Example 10

(2Z,4E)-2-{3-(3-Carboxypropyl)-2-methyl-3-oxopropyl}-4,6,8,10,12-pentamethyltetradec-2,4-dienoic Acid (Compound 12)

(Step 1) In the same manner as Step 1 of Example 7, 1-(4-tert-butoxy-4-oxobutyl) 5-tert-butyl (Z)-2-methyl-4-{(E)-2,4,6,8,10-pentamethyldodec-2-enylidene}pentanedioate (15 mg, 76%) was obtained by using Compound 8 (15 mg, 0.034 mmol) and tert-butyl 4-hydroxybutanoate (6.5 mg, 0.051 mmol).

$^1$H-NMR (CDCl$_3$) δ5.95 (1H, s), 5.27 (1H, d, J=9.2 Hz), 4.08 (2H, td, J=6.4, 1.8 Hz), 2.69-2.58 (2H, m), 2.54-2.44 (1H, m), 2.29 (2H, td, J=7.6, 2.3 Hz), 2.21 (1H, dd, J=13.2, 7.6 Hz), 1.94-1.86 (2H, m), 1.75 (3H, s), 1.49 (9H, s), 1.44 (9H, s), 1.64-1.30 (5H, m), 1.27-1.12 (2H, m), 1.15 (3H, d, J=6.9 Hz), 1.08-0.94 (2H, m), 0.91 (3H, d, J=6.9 Hz), 0.94-0.79 (14H, m).

(Step 2) In the same manner as Step 2 of Example 7, Compound 12 (10.6 mg, 88%) was obtained by using 1-(4-tert-butoxy-4-oxobutyl) 5-tert-butyl (Z)-2-methyl-4-{(E)-2,4,6,8,10-pentamethyldodec-2-enylidene}pentanedioate (15 mg, 0.026 mmol) obtained in Step 1.

¹H-NMR (CDCl₃) δ6.44 (2H, br s), 6.22 (1H, s), 5.32 (1H, d, J=9.5 Hz), 4.18-4.04 (2H, m), 2.71 (1H, dt, J=7.6, 7.0 Hz), 2.62 (1H, dd, J=13.9, 8.0 Hz), 2.55-2.45 (1H, m), 2.45 (2H, td, J=7.3, 2.9 Hz), 2.39 (1H, dd, J=13.9, 6.9 Hz), 2.03-1.92 (2H, m), 1.76 (3H, s), 1.60-1.45 (2H, m), 1.45-1.28 (2H, m), 1.28-1.11 (3H, m), 1.17 (3H, d, J=6.9 Hz), 1.09-0.93 (2H, m), 0.90 (3H, d, J=6.7 Hz), 0.92-0.79 (14H, m).

Example 11

(2Z,4E)-2-{3-(3-Hydroxypropyl)-2-methyl-3-oxopropyl}-4,6,8,10,12-pentamethyltetradec-2,4-dienoic Acid (Compound 13)

(Step 1) In the same manner as Step 1 of Example 7, 1-tert-butyl 5-{3-(tert-butyldimethylsiloxy)propyl}(Z)-4-methyl-2-{(E)-2,4,6,8,10-pentamethyldodec-2-enylidene}pentanedioate (14.9 mg, 63%) was obtained by using Compound 8 (17 mg, 0.039 mmol) and 3-tert-butyldimethylsiloxypropanol (8.9 mg, 0.047 mmol).

¹H-NMR (CDCl₃) δ5.94 (1H, s), 5.27 (1H, d, J=9.4 Hz), 4.16 (2H, td, J=6.7, 1.6 Hz), 3.69 (2H, td, J=6.4, 0.6 Hz), 2.70-2.57 (2H, m), 2.54-2.44 (1H, m), 2.21 (1H, dd, J=13.2, 7.9 Hz), 1.86-1.78 (2H, m), 1.75 (3H, s), 1.50 (9H, s), 1.58-1.45 (2H, m), 1.45-1.31 (2H, m), 1.31-1.12 (3H, m), 1.15 (3H, d, J=6.9 Hz), 1.10-0.95 (2H, m), 0.91 (3H, d, J=6.6 Hz), 0.89 (9H, s), 0.94-0.80 (14H, m), 0.04 (6H, s).

(Step 2) In the same manner as Step 2 of Example 7, Compound 13 (5.9 mg, 61%) was obtained by using 1-tert-butyl 5-{3-(tert-butyldimethylsiloxy)propyl}(Z)-4-methyl-2-{(E)-2,4,6,3,10-pentamethyldodec-2-enylidene}pentanedioate (12.2 mg, 0.022 mmol) obtained in Step 1.

¹H-NMR (CDCl₃) δ6.22 (1H, s), 5.33 (2H, d, J=9.7 Hz), 4.43 (2H, td, J=6.3, 2.3 Hz), 4.23-4.12 (2H, m), 3.71 (1H, br s), 2.75 (1H, dt, J=7.7, 7.1 Hz), 2.63 (1H, dd, J=13.7, 7.3 Hz), 2.57-2.45 (1H, m), 2.40 (1H, dd, J=13.7, 6.9 Hz), 2.12-2.04 (2H, m), 1.90-1.82 (1H, m), 1.77 (3H, s), 1.59-1.47 (2H, m), 1.47-1.31 (2H, m), 1.31-1.11 (2H, m), 1.19 (3H, d, J=6.9 Hz), 1.09-0.93 (2H, m), 0.91 (3H, d, J=6.6 Hz), 0.93-0.80 (14H, m).

Example 12

(2S)-2-{(4Z,6E)-4-Carboxy-2,6,8,10,12,14-hexamethylhexadec-4,6-dienoyloxy}succinic Acid (Compound 14)

(Step 1) In the same manner as Step 1 of Example 7, 1-tert-butyl 5-{(S)-1,4-di-tert-butoxy-1,4-dioxobutan-2-yl}(Z)-4-methyl-2-{(E)-2,4,6,8,10-pentamethyldodec-2-enylidene}pentanedioate (20.7 mg, 68%) was obtained by using Compound 8 (20 mg, 0.046 mmol) and di-tert-butyl L-malate (22.6 mg, 0.092 mmol).

¹H-NMR (CDCl₃) δ5.96 (1H, s), 5.32-5.26 (2H, m), 2.85-2.63 (4H, m), 2.55-2.45 (1H, m), 2.17 (1H, dd, J=14.1, 9.6 Hz), 1.75 (3H, s), 1.63-1.28 (5H, m), 1.49 (9H, s), 1.45 (9H, s), 1.44 (9H, s), 1.17 (3H, d, J=6.9 Hz), 1.27-1.12 (2H, m), 1.08-0.95 (2H, m), 0.91 (3H, d, J=6.6 Hz), 0.93-0.80 (14H, m).

(Step 2) In the same manner as Step 2 of Example 7, Compound 14 (4.6 mg, 31%) was obtained by using 1-tert-butyl 5-{(3)-1,4-di-tert-butoxy-1,4-dioxobutan-2-yl}(Z)-4-methyl-2-{(E)-2,4,6,8,10-pentamethyldodec-2-enylidene}pentanedioate (20 mg, 0.030 mmol) obtained in Step 1.

¹H-NMR (CDCl₃) δ6.11 (1H, s), 5.36 (2H, br s), 5.33 (1H, d, J=9.6 Hz), 5.17 (1H, br s), 3.07 (1H, d, J=15.1 Hz), 2.84 (1H, d, J=15.1 Hz), 2.79-2.58 (2H, m), 2.54-2.43 (1H, m), 2.38-2.26 (1H, m), 1.73 (3H, s), 1.59-1.47 (2H, m), 1.47-1.30 (2H, m), 1.30-1.10 (4H, m), 1.16 (3H, d, J=6.0 Hz), 1.09-0.92 (2H, m), 0.89 (3H, d, J=6.6 Hz), 0.92-0.78 (14H, m).

Example 13

(2Z,4E)-4,6,8,10,12-Pentamethyl-2-[2-methyl-3-oxo-3-{(S)-2-oxotetrahydrofuran-3-yloxy}propyl]tetradec-2,4-dienoic Acid (Compound 15)

(Step 1) In the same manner as Step 1 of Example 7, 1-tert-butyl 5-{(3)-2-oxotetrahydrofuran-3-yl}(Z)-4-methyl-2-{(E)-2,4,6,8,10-pentamethyldodec-2-enylidene}pentanedioate (17.6 mg, 79%) was obtained by using Compound 8 (18.7 mg, 0.043 mmol) and (S)-3-hydroxydihydrofuran-2(3H)-one (5.3 mg, 0.051 mmol).

¹H-NMR (CDCl₃) δ5.97 (1H, s), 5.36 (1H, dd, J=8.9, 8.9 Hz), 5.28 (1H, d, J=9.3 Hz), 4.47 (1H, td, J=9.0, 2.7 Hz), 4.28 (1H, td, J=9.4, 6.0 Hz), 2.79-2.62 (3H, m), 2.44-2.44 (1H, m), 2.32-2.22 (2H, m), 1.75 (3H, s), 1.49 (9H, s), 1.61-1.30 (4H, m), 1.26-1.11 (3H, m), 1.21 (3H, d, J=6.9 Hz), 1.08-0.94 (2H, m), 0.91 (3H, d, J=6.6 Hz), 0.93-0.80 (14H, m).

(Step 2) In the same manner as Step 2 of Example 7, Compound 15 (15.1 mg, quant.) was obtained by using 1-tert-butyl 5-{(S)-2-oxotetrahydrofuran-3-yl}(Z)-4-methyl-2-{(E)-2,4,6,8,10-pentamethyldodec-2-enylidene}pentanedioate (17 mg, 0.033 mmol) obtained in Step 1.

¹H-NMR (CDCl₃) δ6.18 (1H, s), 5.40 (1H, dd, J=9.7, 8.7 Hz), 5.36 (1H, d, J=9.7 Hz), 4.49 (1H, td, J=9.2, 2.3 Hz), 4.34-4.27 (1H, m), 2.38-2.78 (1H, m), 2.74-2.65 (1H, m), 2.63-2.45 (2H, m), 2.36-2.21 (1H, m), 1.76 (3H, s), 1.58-1.45 (2H, m), 1.22 (3H, d, J=6.9 Hz), 1.29-1.12 (6H, m), 1.07-0.94 (2H, m), 0.91 (3H, d, J=6.6 Hz), 0.93-0.79 (14H, m).

Example 14

(2Z,4E)-2-[3-{(S)-3-Carboxy-3-hydroxypropoxy}-2-methyl-3-oxopropyl]-4,6,8,10,12-pentamethyltetradec-2,4-dienoic Acid (Compound 16)

(Step 1) To (S)-3-hydroxydihydrofuran-2(3H)-one (0.5 mL, 6.41 mmol), dichloromethane (6.4 mL), triethylamine (1.34 mL, 9.62 mmol), tert-butyldimethylsilylchloride (1.06 g, 7.07 mmol), and DMAP (39 mg, 0.321 mmol) were added, and the resulting mixture was stirred at room temperature for 3 hours. To the reaction mixture, a saturated aqueous ammonium chloride solution was added, and the resulting mixture was extracted with ethyl acetate. The organic layer was dried over sodium sulfate, and the solvent was evaporated under reduced pressure. To the obtained residue, methanol (11 mL) and sodium methoxide (331 mg, 6.13 mmol) were added, and the resulting mixture was stirred at 50° C. for 2.5 hours. The reaction mixture was cooled to room temperature, and a saturated aqueous ammonium chloride solution was added thereto, and then, the resulting mixture was extracted with ethyl acetate. The organic layer was dried over sodium sulfate, and the solvent was evaporated under reduced pressure. The resulting residue was purified by silica gel column chromatography (ethyl acetate/n-hexane=0/100 to 30/70), whereby methyl (S)-2-(tert-butyldimethylsiloxy)-4-hydroxybutanoate (225 mg, 14%) was obtained.

¹H-NMR (CDCl₃) δ4.45 (1H, dd, J=6.8, 4.9 Hz), 3.83-3.74 (2H, m), 3.74 (3H, s), 2.06-1.92 (3H, m), 0.92 (9H, s), 0.11 (3H, s), 0.08 (3H, s).

(Step 2) To methyl (S)-2-(tert-butyldimethylsiloxy)-4-hydroxybutanoate (220 mg, 0.886 mmol) obtained in Step 1, dichloromethane (0.89 mL), diisopropylethylamine (0.464 mL, 2.66 mmol), and {(chloromethoxy)methyl}benzene (0.30 mL, 2.21 mmol) were added, and the resulting mixture was stirred at room temperature for 1.5 hours. To the reaction mixture, a saturated aqueous ammonium chloride solution was added, and the resulting mixture was extracted with ethyl acetate. The organic layer was dried over sodium sulfate, and the solvent was evaporated under reduced pressure. The resulting residue was purified by silica gel column chromatography (ethyl acetate/n-hexane=20/80), whereby methyl (S)-4-(benzyloxymethoxy)-2-(tert-butyldimethylsiloxy)butanoate (191 mg, 59%) was obtained, ¹H-NMR (CDCl₃) δ7.36-7.27 (5H, m), 4.74 (1H, d, J=6.6 Hz), 4.71 (1H, d, J=6.6 Hz), 4.63 (1H, d, J=11.8 Hz), 4.57 (1H, d, J=11.8 Hz), 4.38 (1H, dd, J=7.6, 4.6 Hz), 3.73-3.72 (1H, m), 3.72 (3H, s), 3.69-3.63 (1H, m), 2.09-1.93 (2H, m), 0.91 (9H, s), 0.09 (3H, s), 0.06 (3H, s).

(Step 3) To methyl (S)-4-(benzyloxymethoxy)-2-(tert-butyldimethylsiloxy)butanoate (190 mg, 0.52 mmol) obtained in Step 2, acetonitrile (10 mL) and an aqueous sodium hydroxide solution (0.5 mol/L, 5.2 mL, 2.58 mmol) were added, and the resulting mixture, was stirred at room temperature for 5.5 hours. To the reaction mixture, Dowex 50 (registered trademark) (Muromachi Technos, 50WX8, 50-100 mesh, H⁺ form) was added thereto to neutralize the mixture, and the insoluble matter was removed by filtration, and then, the filtrate was extracted with ethyl acetate. The organic layer was washed with saturated brine and dried over sodium sulfate, and then, the solvent was evaporated under reduced pressure, whereby (S)-4-(benzyloxymethoxy)-2-(tert-butyldimethylsiloxy)butanoic acid (156 mg) was obtained.

(Step 4) To N,N'-diisopropylcarbodiimide (0.643 mL, 4.13 mmol), tert-butanol (0.415 mL, 4.34 mmol) and copper(I) chloride (20 mg, 0.21 mmol) were added, and the resulting mixture was stirred at room temperature for 16 hours. The reaction mixture was filtered, through Celite (registered trademark), and the solvent in the filtrate was evaporated under reduced pressure. To the obtained residue, dichloromethane (7.4 mL) and (S)-4-(benzyloxymethoxy)-2-(tert-butyldimethylsiloxy)butanoic acid (183 mg, 0.516 mmol) obtained in Step 3 were added, and the resulting mixture was stirred at room temperature for 24 hours. The reaction mixture was filtered through Celite (registered trademark), and the solvent of the filtrate was evaporated under reduced pressure. The resulting residue was purified by thin-layer chromatography (ethyl acetate/n-hexane=1/20), whereby tert-butyl (S)-4-(benzyloxymethoxy)-2-(tert-butyldimethylsiloxy)butanoate (40 mg, 19%) was obtained.

¹H-NMR (CDCl₃) δ7.38-7.26 (5H, m), 4.75 (1H, d, J=6.7 Hz), 4.72 (1H, d, J=6.7 Hz), 4.63 (1H, d, J=12.0 Hz), 4.58 (1H, d, J=12.0 Hz), 4.22 (1H, dd, J=7.9, 4.4 Hz), 3.77-3.71 (1H, m), 3.69-3.63 (1H, m), 2.01-1.89 (2H, m), 1.47 (9H, s), 0.91 (9H, s), 0.10 (3H, s), 0.06 (3H, s).

(Step 5) To tert-butyl (S)-4-(benzyloxymethoxy)-2-(tert-butyldimethylsiloxy) butanoate (40 mg, 0.097 mmol) obtained in Step 4, methanol (2 mL) and palladium/carbon (10%, 10.4 mg, 0.001 mmol) were added, and the resulting mixture was stirred at room temperature in a hydrogen atmosphere for 10.5 hours. The reaction mixture was filtered through Celite (registered trademark), and the solvent in the filtrate was evaporated under reduced pressure, whereby tert-butyl (S)-2-(tert-butyldimethylsiloxy)-4-hydroxybutanoate (25.5 mg, 90%) was obtained.

¹H-NMR (CDCl₃) δ4.30 (1H, dd, J=6.6, 4.8 Hz), 3.78 (2H, t, J=5.9 Hz), 2.21 (1H, s), 2.03-1.89 (2H, m), 1.47 (9H, s), 0.92 (9H, s), 0.11 (3H, 3), 0.07 (3H, s).

(Step 6) In the same manner as Step 1 of Example 7, 1-{(S)-4-tert-butoxy-3-(tert-butyldimethylsiloxy)-4-oxobutyl} 5-tert-butyl (Z)-2-methyl-4-{(E)-2,4,6,8,10-pentamethyldodec-2-enylidene}pentanedioate (13.6 mg, 47%) was obtained by using Compound 8 (18 mg, 0.041 mmol) and tert-butyl (S)-2-(tert-butyldimethylsiloxy)-4-hydroxybutanoate (25 mg, 0.086 mmol) obtained in Step 5.

¹H-NMR (CDCl₃) δ5.95 (1H, s), 5.28 (1H, d, J=9.0 Hz), 4.27-4.08 (3H, m), 2.73-2.58 (2H, m), 2.55-2.44 (1H, m), 2.20 (1H, dd, J=13.5, 8.6 Hz), 2.09-2.00 (1H, m), 1.95-1.85 (1H, m), 1.75 (3H, s), 1.49 (9H, s), 1.47 (9H, s), 1.59-1.43 (2H, m), 1.43-1.30 (2H, m), 1.30-1.11 (3H, m), 1.15 (3H, d, J=6.9 Hz), 1.08-0.93 (2H, m), 0.92 (3H, d, J=6.6 Hz), 0.90 (9H, s), 0.92-0.80 (14H, m), 0.09 (3H, s), 0.04 (3H, s).

(Step 7) To 1-{(S)-4-tert-butoxy-3-(tert-butyldimethylsiloxy)-4-oxobutyl}5-tert-butyl (Z)-2-methyl-4-{(E)-2,4,6,8,10-pentamethyldodec-2-enylidene}pentanedioate (13 mg, 0.018 mmol) obtained in Step 6, methanol (0.92 mL) and ammonium fluoride (6.8 mg, 0.18 mmol) were added, and the resulting mixture was stirred at room temperature for 54 hours. The solvent was evaporated under reduced pressure, and then, the resulting residue was purified by thin-layer chromatography (ethyl acetate/n-hexane=1/4), whereby 1-{ (S)-4-tert-butoxy-3-hydroxy-4-oxobutyl}5-tert-butyl (Z)-2-methyl-4-{(E)-2,4,6,8,10-pentamethyldodec-2-enylidene}pentanedioate (8.2 mg, 75%) was obtained.

¹H-NMR (CDCl₃) δ5.96 (1H, s), 5.28 (1H, d, J=9.5 Hz), 4.27-4.18 (2H, m), 4.15-4.09 (1H, m), 2.88 (1H, dd, J=5.5 Hz), 2.71-2.58 (2H, m), 2.54-2.44 (1H, m, 2.22 (1H, dd, J=13.0, 7.8 Hz), 2.15-2.06 (1H, m), 1.89-1.80 (1H, m), 1.75 (3H, s), 1.50 (9H, s), 1.50 (9H, s), 1.61-1.45 (2H, m), 1.45-1.30 (2H, m), 1.28-1.12 (3H, m), 1.16 (3H, d, J=6.9 Hz), 1.08-0.93 (2H, m), 0.91 (3H, d, J=6.5 Hz), 0.93-0.80 (14H, m).

(Step 8) In the same manner as Step 2 of Example 7, Compound 16 (2.3 mg, 35%) was obtained by using 1-{(S)-4-tert-butoxy-3-hydroxy-4-oxobutyl}5-tert-butyl (Z)-2-methyl-4-{(E)-2,4,6,8,10-pentamethyldodec-2-enylidene}pentanedioate (8.2 mg, 0.014 mmol) obtained in Step 7.

¹H-NMR (CD₃OD) δ6.10 (1H, s), 5.51-5.26 (2H, m), 4.64-4.27 (5H, m), 2.81-2.48 (2H, m), 2.39-2.23 (2H, m), 2.23-2.12 (1H, m), 2.09-1.99 (1H, m), 1.79 (3H, s), 1.57-1.15 (5H, m), 1.20 (3H, d, J=6.6 Hz), 1.13-1.00 (2H, m), 0.92 (3H, d, J=6.6 Hz), 0.95-0.81 (14H, m).

Example 15

(2S,3S)-2-{(4Z,6E)-4-Carboxy-2,6,8,10,12,14-hexamethylhexadec-4,6-dienoyloxy}-3-(diethoxyphosphoryloxy)succinic Acid (Compound 17)

(Step 1) To di-tert-butyl tartrate (182 mg, 0.692 mmol), dichloromethane (1.73 mL), triethylamine (0.145 mL, 1.04 mmol), and diethylchlorophosphoric acid (0.050 mL, 0.346 mmol) were added, and the resulting mixture was stirred at room temperature for 20 hours. To the reaction mixture, water was added, and the resulting mixture was extracted with chloroform. The organic layer was dried, over sodium sulfate, and the solvent was evaporated under reduced pressure. The resulting residue was purified by silica, gel column chromatography (ethyl acetate/n-hexane=5/95 to 30/70), whereby di-tert-butyl (2R,3R)-2-(diethoxyphosphoryloxy)-3-hydroxysuccinate (46 mg, 33%) was obtained.

$^1$H-NMR (CDCl$_3$) δ5.03 (1H, dd, J=9.1, 2.2 Hz), 4.50 (1H, dt, J=7.5, 2.2 Hz), 4.28-4.18 (2H, m), 4.15-4.00 (2H, m), 3.12 (1H, d, J=7.9 Hz), 1.53 (9H, s), 1.51 (9H, s), 1.33 (3H, td, J=7.1, 1.0 Hz), 1.30 (3H, td, J=7.1, 1.0 Hz).

(Step 2) In the same manner as Step 1 of Example 7, 1-tert-butyl 5-{(2S,3S)-3-(diethoxyphosphoryloxy)-1,4-di-tert-butoxy-1,4-dioxobutan-2-yl}(Z)-4-methyl-2-{(E)-2,4,6,8,10-pentamethyldodec-2-enylidene}pentanedioate (30 mg, 80%) was obtained by using Compound 8 (20 mg, 0.046 mmol) and di-tert-butyl (2R,3R)-2-(diethoxyphosphoryloxy)-3-hydroxysuccinate (36.5 mg, 0.092 mmol) obtained in Step 1.

$^1$H-NMR (CDCl$_3$) δ5.96 (1H, s), 5.50 (1H, t, J=2.4 Hz), 5.29 (1H, d, J=9.5 Hz), 5.27 (1H, dd, J=9.0, 2.4 Hz), 4.29-4.21 (2H, m), 4.14-4.05 (2H, m), 2.79 (1H, ddd, J=13.6, 4.8, 0.8 Hz), 2.75-2.66 (1H, m), 2.55-2.44 (1H, m), 2.14 (1H, dd, J=13.6, 9.5 Hz), 1.75 (3H, d, J=0.8 Hz), 1.50 (9H, s), 1.48 (9H, s), 1.44 (9H, s), 1.58-1.10 (7H, m), 1.35 (3H, td, J=7.1, 1.1 Hz), 1.30 (3H, td, J=7.1, 1.1 Hz), 1.22 (3H, d, J=7.0 Hz), 1.08-0.93 (2H, m), 0.91 (3H, d, J=6.5 Hz), 0.94-0.78 (14H, m).

(Step 3) In the same manner as Step 2 of Example 7, Compound 17 (8.0 mg, 39%) was obtained by using 1-tert-butyl 5-{(2S,3S)-3-(diethoxyphosphoryloxy)-1,4-di-tert-butoxy-1,4-dioxobutan-2-yl}(Z)-4-methyl-2-{(E)-2,4,6,8,10-pentamethyldodec-2-enylidene}pentanedioate (25 mg, 0.031 mmol).

$^1$H-NMR (CDCl$_3$) δ6.06 (1H, s), 5.67-5.49 (1H, m), 5.42-5.25 (2H, m), 4.29-4.04 (5H, m), 3.11 (1H, q, J=7.4 Hz), 2.85-2.72 (2H, m), 2.54-2.44 (1H, m), 2.41-2.18 (1H, m), 1.77 (3H, s), 1.59-1.10 (14H, m), 1.10-0.93 (2H, m), 0.93-0.76 (17H, m).

Example 16

(2Z,4E)-2-[3-{(R)-1-Carboxypropyl}-2-methyl-3-oxopropyl]-4,6,8,10,12-pentamethyltetradec-2,4-dienoic Acid (Compound 18)

(Step 1) In the same manner as Step 1 of Example 7, 1-{(R)-1-tert-butoxy-1-oxobutan-2-yl}5-tert-butyl (Z)-2-methyl-4-{(E)-2,4,6,8,10-pentamethyldodec-2-enylidene}pentanedioate (12 mg, 51%) was obtained by using Compound 8 (18 mg, 0.041 mmol) and tert-butyl (R)-2-hydroxybutanoate (7.3 mg, 0.045 mmol).

$^1$H-NMR (CDCl$_3$) δ5.97 (1H, s), 5.27 (1H, d, J=9.6 Hz), 4.80 (1H, dd, J=7.3, 4.7 Hz), 2.76-2.65 (2H, m), 2.54-2.43 (1H, m), 2.29-2.20 (1H, m), 1.90-1.77 (2H, m), 1.74 (3H, s), 1.59-1.30 (5H, m), 1.49 (9H, s), 1.45 (9H, s), 1.27-1.11 (2H, m), 1.14 (3H, d, J=6.3 Hz), 1.08-0.93 (2H, m), 0.97 (3H, t, J=7.5 Hz), 0.91 (3H, d, J=6.7 Hz), 0.93-0.79 (14H, m).

(Step 2) In the same manner as Step 2 of Example 7, Compound 18 (8.6 mg, 71%) was obtained by using 1-{(R)-1-tert-butoxy-1-oxobutan-2-yl}5-tert-butyl (Z)-2-methyl-4-{(E)-2,4,6,8,10-pentamethyldodec-2-enylidene}pentanedioate (12.2 mg, 0.026 mmol) obtained in Step 1.

$^1$H-NMR (CDCl$_3$) δ6.22 (1H, s), 6.04 (2H, br s), 5.33 (1H, d, J=9.7 Hz), 5.00-4.93 (1H, m), 2.81 (1H, q, J=7.3 Hz), 2.69 (1H, dd, J=13.7, 7.6 Hz), 2.54-2.45 (1H, m), 2.42 (1H, dd, J=14.6, 7.0 Hz), 1.98-1.83 (2H, m), 1.76 (3H, s), 1.59-1.46 (2H, m), 1.46-1.12 (5H, m), 1.22 (3H, d, J=6.9 Hz), 1.08-0.94 (2H, m), 1.00 (3H, t, J=7.4 Hz), 0.90 (3H, d, J=6.6 Hz), 0.92-0.79 (14H, m).

Example 17

(2Z,4E)-2-[3-{(R)-2,3-Dihydroxypropyl}-2-methyl-3-oxopropyl]-4,6,8,10,12-pentamethyltetradec-2,4-dienoic Acid (Compound 19)

(Step 1) In the same manner as Step 1 of Example 7, 1-tert-butyl 5-{(R)-2,2-dimethyl-1,3-dioxolan-4-yl}methyl (Z)-4-methyl-2-{(E)-2,4,6,8,10-pentamethyldodec-2-enylidene}pentanedioate (16.9 mg, 67%) was obtained by using Compound 8 (20 mg, 0.046 mmol) and (3)-(2,2-dimethyl-1,3-dioxolan-4-yl)methanol (7.3 mg, 0.055 mmol).

$^1$H-NMR (CDCl$_3$) δ5.95 (1H, s), 5.27 (1H, d, J=9.4 Hz), 4.32-4.25 (1H, m), 4.15-4.08 (2H, m), 4.05 (1H, dd, J=8.5, 6.6 Hz), 3.74 (1H, dd, J=8.5, 6.0 Hz), 2.72-2.62 (2H, m), 2.54-2.44 (1H, m), 2.28-2.20 (1H, m), 1.75 (3H, s), 1.49 (9H, s), 1.42 (3H, s), 1.35 (3H, s), 1.60-1.31 (5H, m), 1.26-1.13 (2H, m), 1.17 (3H, d, J=6.9 Hz), 1.08-0.95 (2H, m), 0.91 (3H, d, J=6.6 Hz), 0.93-0.80 (14H, m).

(Step 2) In the same manner as Step 2 of Example 7, Compound 19 (13.1 mg, 96%) was obtained by using 1-tert-butyl 5-{(R)-2,2-dimethyl-1,3-dioxolan-4-yl}methyl (Z)-4-methyl-2-{(E)-2,4,6,8,10-pentamethyldodec-2-enylidene}pentanedioate (16.5 mg, 0.030 mmol).

$^1$H-NMR (CDCl$_3$) δ5.94 (1H, s), 5.29 (1H, d, J=9.5 Hz), 4.37 (1H, dd, J=11.3, 4.1 Hz), 3.93 (1H, dd, J=11.7, 7.2 Hz), 3.83-3.77 (1H, m), 3.64 (1H, dd, J=11.3, 4.1 Hz), 3.56 (1H, dd, J=11.7, 5.4 Hz), 2.71-2.59 (1H, m), 2.54-2.44 (2H, m), 2.40 (1H, dd, J=14.0, 10.2 Hz), 1.73 (3H, s), 1.59-1.46 (2H, m), 1.46-1.30 (2H, m), 1.24-1.11 (3H, m), 1.18 (3H, d, J=6.8 Hz), 1.09-0.92 (2H, m), 0.90 (3H, d, J=6.5 Hz), 0.92-0.80 (14H, m).

Example 18

(2Z,4E)-4,6,8,10,12-Pentamethyl-2-[2-methyl-3-oxo-3-{(R)-2-oxotetrahydrofuran-3-yloxy}propyl]tetradec-2,4-dienoic Acid (Compound 20)

(Step 1) In the same manner as Step 1 of Example 7, 1-tert-butyl 5-{(R)-2-oxotetrahydrofuran-3-yl}(Z)-4-methyl-2-{(E)-2,4,6,8,10-pentamethyldodec-2-enylidene}pentanedioate (16.1 mg, 68%) was obtained by using Compound 8 (20 mg, 0.046 mmol) and (R)-3-hydroxydihydrofuran-2(3H)-one (5.6 mg, 0.055 mmol).

$^1$H-NMR (CDCl$_3$) δ5.95 (1H, s), 5.45-5.40 (1H, m), 5.28 (1H, d, J=9.5 Hz), 4.47 (1H, dd, J=11.1, 5.1 Hz), 4.33 (1H, d, J=11.1 Hz), 2.83 (1H, dd, J=18.4, 6.8 Hz), 2.67 (1H, q, J=7.5 Hz), 2.62-2.45 (3H, m), 2.31 (1H, dd, J=13.8, 7.2 Hz), 1.75 (3H, s), 1.59-1.45 (2H, m), 1.49 (9H, s), 1.45-1.30 (2H, m), 1.28-1.11 (3H, m), 1.17 (3H, d, J=6.9 Hz), 1.09-0.94 (2H, m), 0.91 (3H, d, J=6.6 Hz), 0.93-0.80 (14H, m).

(Step 2) In the same manner as Step 2 of Example 7, Compound 20 (12.4 mg, 87%) was obtained by using 1-tert-butyl 5-{(R)-2-oxotetrahydrofuran-3-yl}(Z)-4-methyl-2-{(E)-2,4,6,8,10-pentamethyldodec-2-enylidene}pentanedioate (16 mg, 0.031 mmol) obtained in Step 1.

$^1$H-NMR (CDCl$_3$) δ6.24 (1H, s), 5.44-5.39 (1H, m), 5.34 (1H, d, J=9.5 Hz), 4.47 (1H, dd, J=10.9, 5.0 Hz), 4.33 (1H, d, J=10.9 Hz), 2.84 (1H, dd, J=18.3, 6.9 Hz), 2.77 (1H, q, J=6.9 Hz), 2.64-2.56 (2H, m), 2.56-2.46 (1H, m), 2.46-2.39 (1H, m), 1.77 (3H, s), 1.59-1.46 (2H, m), 1.46-1.29 (2H, m), 1.29-1.10 (3H, m), 1.19 (3H, d, J=7.0 Hz), 1.09-0.94 (2H, m), 0.91 (3H, d, J=6.6 Hz), 0.93-0.80 (14H, m).

Example 19

(2Z,4E)-4,6,8,10,12-Pentamethyl-2-[2-methyl-3-oxo-3-{(S)-5-oxotetrahydrofuran-3-yl}propyl]tetradec-2,4-dienoic Acid (Compound 21)

(Step 1) In the same manner as Step 1 of Example 7, 1-tert-butyl 5-{(S)-5-oxotetrahydrofuran-3-yl}(Z)-4-methyl-2-{(E)-2,4,6,8,10-pentamethyldodec-2-enylidene}pentanedioate (14.3 mg, 60%) was obtained by using Compound 8 (20 mg, 0.046 mmol) and (S)-4-hydroxydihydrofuran-2(3H)-one (5.6 mg, 0.055 mmol).

$^1$H-NMR (CDCl$_3$) δ5.95 (1H, d, J=0.8 Hz), 5.45-5.41 (1H, m), 5.28 (1H, dt, J=9.4, 1.2 Hz), 4.47 (1H, dd, J=10.9, 4.9 Hz), 4.33 (1H, d, J=10.9 Hz), 2.34 (1H, dd, J=18.3, 7.1 Hz), 2.72-2.63 (1H, m), 2.61-2.44 (3H, m), 2.31 (1H, ddd, J=13.7, 7.1, 0.8 Hz), 1.74 (3H, d, J=1.2 Hz), 1.60-1.46 (2H, m), 1.49 (9H, s), 1.45-1.31 (2H, m), 1.27-1.12 (3H, m), 1.17 (3H, d, J=6.9 Hz), 1.09-0.93 (2H, m), 0.91 (3H, d, J=6.6 Hz), 0.93-0.80 (14H, m).

(Step 2) In the same, manner as Step 2 of Example 7, Compound 21 (12.2 mg, 98%) was obtained by using 1-tert-butyl 5-{(S)-5-oxotetrahydrofuran-3-yl}(Z)-4-methyl-2-{(E)-2,4,6,8,10-pentamethyldodec-2-enylidene}pentanedioate (14 mg, 0.027 mmol) obtained in Step 1.

$^1$H-NMR (CDCl$_3$) δ6.23 (1H, s), 5.49-5.39 (1H, m), 5.34 (1H, d, J=9.6 Hz), 4.47 (1H, dd, J=11.0, 5.1 Hz), 4.33 (1H, d, J=11.1 Hz), 2.84 (1H, dd, J=18.6, 6.9 Hz), 2.81-2.73 (1H, m), 2.64-2.56 (2H, m), 2.56-2.46 (1H, m), 2.43 (1H, dd, J=13.9, 6.7 Hz), 1.77 (3H, s), 1.59-1.47 (2H, m), 1.45-1.31 (2H, m), 1.28-1.13 (3H, m), 1.19 (3H, d, J=6.9 Hz), 1.08-0.94 (2H, m), 0.91 (3H, d, J=6.6 Hz), 0.93-0.80 (14H, m).

Example 20

2-{(4Z,6E)-4-Carboxy-2,6,8,10,12,14-hexamethylhexadec-4,6-dienoyloxy}malonic Acid (Compound 22)

To di-tert-butyl malonate (0.207 mL, 0.925 mmol), THF (40 mL) and DBU (0.139 mL, 0.925) were added, and the resulting mixture was stirred at room temperature for 1 hour. The reaction mixture was cooled to −20° C., and carbon tetrabromide (207 mg, 0.925 mmol) was added thereto, and the resulting mixture was stirred at −20° C. for 2 hours. To the reaction mixture, a saturated aqueous ammonium chloride solution was added, and the resulting mixture was extracted with chloroform. The organic layer was dried over sodium sulfate, and the solvent was evaporated under reduced pressure. To a portion (80 mg) of the obtained residue, DMF (1.43 mL), Compound 8 (12.5 mg, 0.029 mmol), and potassium carbonate (11.9 mg, 0.086 mmol) were added, and the resulting mixture was stirred at room temperature for 2 hours. To the reaction mixture, a saturated aqueous ammonium chloride solution was added, and the resulting mixture was extracted with ethyl acetate. The organic layer was dried over sodium sulfate, and the solvent was evaporated under reduced pressure. The resulting residue was purified by thin-layer chromatography (ethyl acetate/n-hexane=1/9). By using the obtained residue, Compound 22 (1.1 mg) was obtained in the same manner as Step 2 of Example 7.

$^1$H-NMR (CD$_2$OD) δ5.96 (1H, s), 5.28 (1H, d, J=9.5 Hz), 4.55 (1H, s), 2.72-2.49 (3H, m), 2.35-2.26 (1H, m), 1.80 (3H, s), 1.65-1.00 (9H, m), 1.15 (3H, d, J=6.9 Hz), 1.15 (3H, d, J=6.9 Hz), 0.92 (3H, d, J=6.5 Hz), 0.93-0.82 (14H, m).

Example 21

2-{(4Z,6E)-4-Carboxy-2,6,8,10,12,14-hexamethylhexadec-4,6-dienoyloxy}ethane-1,1,2-tricarboxylic Acid (Compound 23)

(Step 1) In the same manner as Step 1 of Example 7, tri-tert-butyl 2-{(4Z,6E)-4-(tert-butoxycarbonyl)-2,6,8,10,12,14-hexamethylhexadec-4,6-dienoyloxy}ethane-1,1,2-tricarboxylate (12.0 mg, 53%) was obtained by using Compound 8 (13 mg, 0.030 mmol) and tri-tert-butyl 2-hydroxyethane-1,1,2-tricarboxylate (20.6 mg, 0.060 mmol).

$^1$H-NMR (CDCl$_3$) δ5.96 (1H, s), 5.55 (1H, dd, J=6.0, 3.8 Hz), 5.30 (1H, dd, J=9.4, 4.2 Hz), 3.83 (1H, d, J=5.7 Hz), 2.89-2.76 (1H, m), 2.71-2.62 (1H, m), 2.55-2.44 (1H, m), 2.20-2.11 (1H, m), 1.75 (3H, s), 1.63-1.30 (39H, m), 1.28-1.12 (7H, m), 1.08-0.95 (2H, m), 0.91 (3H, d, J=6.9 Hz), 0.93-0.80 (14H, m).

(Step 2) In the same manner as Step 2 of Example 7, Compound 23 (5.0 mg, 59%) was obtained by using tri-tert-butyl 2-{(4Z,6E)-4-(tert-butoxycarbonyl)-2,6,8,10,12,14-hexamethylhexadec-4,6-dienoyloxy}ethane-1,1,2-tricarboxylate (12 mg, 0.016 mmol) obtained in Step 1, $^1$H-NMR (CDCl$_3$) δ6.18 (1H, s), 5.35 (1H, d, J=9.5 Hz), 2.71-2.60 (3H, m), 2.56-2.45 (1H, m), 1.78 (3H, s), 1.59-1.47 (2H, m), 1.47-1.30 (3H, m), 1.28-1.12 (4H, m), 1.20 (3H, d, J=6.4 Hz), 1.09-0.96 (2H, m), 0.91 (3H, d, J=6.7 Hz), 0.93-0.79 (14H, m).

Example 22

2-[{(4Z,6E)-4-Carboxy-2,6,8,10,12,14-hexamethylhexadec-4,6-dienoyloxy}methyl]succinic Acid (Compound 24)

(Step 1) In the same manner as Step 1 of Example 7, 1-{4-tert-butoxy-2-(tert-butoxycarbonyl)-4-oxobutyl}(Z)-2-methyl-4-{(E)-2,4,6,8,10-pentamethyldodec-2-enylidene}pentanedioate (30.9 mg, 99%) was obtained by using Compound 8 (20 mg, 0.046 mmol) and di-tert-butyl 2-(hydroxymethyl)succinate (23.9 mg, 0.092 mmol).

$^1$H-NMR (CDCl$_3$) δ5.93 (1H, s), 5.27 (1H, dd, J=9.5, 1.0 Hz), 4.32-4.17 (2H, m), 3.05-2.97 (1H, m), 2.72-2.57 (3H, m), 2.54-2.44 (1H, m), 2.39 (1H, dt, J=16.8, 6.0 Hz), 2.17 (1H, ddd, J=13.8, 8.4, 3.2 Hz), 1.74 (3H, s), 1.48 (9H, s), 1.58-1.46 (2H, m), 1.46-1.29 (3H, m), 1.44 (18H, s), 1.28-1.11 (2H, m), 1.15 (3H, d, J=6.9 Hz), 1.08-0.95 (2H, m), 0.91 (3H, d, J=6.6 Hz), 0.89-0.80 (14H, m).

(Step 2) In the same manner as Step 2 of Example 7, Compound 24 (5.8 mg, 26%) was obtained by using 1-{4-tert-butoxy-2-(tert-butoxycarbonyl)-4-oxobutyl}(Z)-2-methyl-4-{(E)-2,4,6,8,10-pentaraethyldodec-2-enylidene}pentanedioate (30 mg, 0.044 mmol) obtained in Step 1.

$^1$H-NMR (CDCl$_3$) δ6.21 (1H, s), 5.76 (3H, br s), 5.33 (1H, d, J=9.5 Hz), 4.44-4.23 (2H, m), 3.26-3.12 (1H, m), 2.91-2.78 (1H, m), 2.77-2.44 (4H, m), 2.42-2.29 (1H, m), 1.75 (3H, s), 1.59-1.47 (2H, m), 1.47-1.31 (3H, m), 1.31-1.10 (2H, m), 1.16 (3H, d, J=6.9 Hz), 1.09-0.94 (2H, m), 0.90 (3H, d, J=6.6 Hz), 0.93-0.79 (14H, m).

Example 23

(2S)-2-{(4Z,6E)-4-Carboxy-2,6,8,10,12,14-hexamethylhexadec-4,6-dienamide}succinic Acid (Compound 25)

(Step 1) To Compound 8 (10 mg, 0.023 mmol), THF (1.1 mL), triethylamine (0.019 mL, 0.14 mmol), di-tert-butyl L-aspartate hydrochloride (12.9 mg, 0.046 mmol), EDC-HCl (8.8 mg, 0.046 mmol), and 1-hydroxybenzotriazole monohydrate (3.9 mg, 0.025 mmol) were added, and the resulting mixture was stirred at room temperature for 19 hours. To the reaction mixture, water was added, and the resulting mixture was extracted with ethyl acetate. The organic layer was washed with saturated brine and dried over sodium sulfate, and then, the solvent was evaporated under reduced pressure. The resulting residue was purified by thin-layer column chromatography (ethyl acetate/n-hexane=1/3), whereby di-tert-butyl (2S)-2-{(4Z,6E)-4-(tert-butoxycarbonyl)-2,6,8,10,12,14-hexamethylhexadec-4,6-dienamide}succinate (13.6 mg, 89%) was obtained.

$^1$H-NMR (CDCl$_3$) δ6.54 (1H, d, J=7.6 Hz), 5.95 (1H, s), 5.28 (1H, d, J=9.5 Hz), 4.61 (1H, dt, J=7.6, 4.5 Hz), 2.84 (1H, dd, J=16.9, 4.5 Hz), 2.74 (1H, dd, J=16.9, 4.5 Hz), 2.64 (1H, ddd, J=13.8, 6.1, 1.0 Hz), 2.53-2.43 (2H, m), 2.20 (1H, ddd, J=13.8, 6.1, 1.0 Hz), 1.74 (3H, d, J=1.0 Hz), 1.59-1.47 (2H, m), 1.51 (9H, s), 1.47-1.30 (2H, m), 1.45 (9H, s), 1.43 (9H, s), 1.28-1.10 (3H, m), 1.14 (3H, d, J=6.9 Hz), 1.09-0.93 (2H, m), 0.90 (3H, d, J=6.6 Hz), 0.92-0.80 (14H, m).

(Step 2) In the same manner as Step 2 of Example 7, Compound 25 (3.8 mg, 39%) was obtained by using di-tert-butyl (2S)-2-{(4Z,6E)-4-(tert-butoxycarbonyl)-2,6,8,10,12,14-hexamethylhexadec-4,6-dienamide}succinate (13 mg, 0.020 mmol) obtained in Step 1.

$^1$H-NMR (CDCl$_3$) δ7.48 (1H, br s), 6.12 (1H, s), 5.31 (1H, d, J=9.0 Hz), 4.82-4.73 (2H, m), 4.17 (3H, br s), 2.99-2.75 (2H, m), 2.71-2.41 (3H, m), 1.71 (3H, s), 1.58-1.00 (9H, m), 1.08 (3H, d, J=6.4 Hz), 0.92-0.78 (17H, m).

Example 24

(2S)-2-{(4Z,6E)-4-Carboxy-2,6,8,10,12,14-hexamethylhexadec-4,6-dienamide}propane-1,3-dicarboxylic Acid (Compound 26)

(Step 1) To Compound 2 (34.8 mg, 0.091 mmol), DMF (1.0 mL), L-glutamic acid di-tert-butyl ester hydrochloride (13.1 mg, 0.055 mmol), 1-hydroxybenzotriazole hydrate (12.2 mg, 0.080 mmol), triethylamine (0.025 mL, 0.179 mmol), and EDC-HCl (17.3 mg, 0.090 mmol) were added, and the resulting mixture was stirred at room temperature for 2 hours. The reaction mixture was poured into 1 mol/L hydrochloric acid, and the resulting mixture was extracted with ethyl acetate. The organic layer was washed with saturated brine and dried over anhydrous sodium sulfate, and then, the solvent was evaporated, under reduced pressure. The resulting residue was purified by silica gel preparative thin-layer chromatography (chloroform/methanol), whereby di-tert-butyl (2S)-2-{(4Z,6E)-4-carboxy-2,6,8,10,12,14-hexamethylhexadec-4,6-dienamide}propane-1,3-dicarboxylate (15.4 mg, 27%) was obtained.

(Step 2) To di-tert-butyl (2S)-2-{(4Z,6E)-4-carboxy-2,6,8,10,12,14-hexamethylhexadec-4,6-dienamide}propane-1,3-dicarboxylate (15.4 mg, 0.0247 mmol) obtained in Step 1, dichloromethane (1 mL) and trifluoroacetic acid (1 mL) were added, and the resulting mixture was stirred at room temperature for 1 hour. The solvent was evaporated under reduced pressure. The resulting residue was purified by high performance, liquid chromatography (column: Waters SunFire C18, 19×250 mm; mobile phase: acetonitrile containing 0.1% TFA/water containing 0.1% TFA), whereby Compound 26 (11.1 mg, 88%) was obtained.

$^1$H NMR (CD$_3$OD) δ6.05 (1H, s), 5.29 (1H, d, J=9.6 Hz), 4.39 (1H, dd, J=8.9, 5.0 Hz), 2.64 (1H, m), 2.61 (1H, m), 2.53 (1H, m), 2.38 (2H, m), 2.26 (1H, m), 2.17 (1H, m), 1.94 (1H, m), 1.76 (3H, d, J=1.1 Hz), 1.54 (1H, m), 1.52 (1H, m), 1.39 (2H, m), 1.21 (2H, m), 1.13 (3H, d, J=6.7 Hz), 1.05 (2H, m), 0.91 (3H, d, J=6.6 Hz), 0.90-0.75 (14H, m).

Example 25

Di(acetoxymethyl) 4-{(4Z,6E)-4-(acetoxymethoxycarbonyl)-2,6,8,10,12,14-hexamethylhexadec-4,6-dienoyloxy}-5-oxotetrahydrofuran-2,3-dicarboxylate (Compound 27)

Bis(acetoxymethyl) (Z)-2-methyl-4-{(E)-2,4,6,8,10-pentamethyldodec-2-enylidene}pentanedioate (Compound 29)

To Compound 1 (130 mg, 0.235 mmol), water (10 mL), sodium hydrogen carbonate (200 mg, 2.33 mmol), chloroform (5 mL), tetrabutylammonium hydrogen sulfate (80 mg, 0.235 mmol), and bromomethyl acetate (0.120 mL, 1.22 mmol) were added, and the resulting mixture was vigorously stirred at room temperature for 3 hours. To the reaction mixture, a saturated aqueous ammonium chloride solution was added, and the resulting mixture was extracted with chloroform. The organic layer was washed with saturated brine and dried over anhydrous magnesium sulfate, and then, the solvent was evaporated under reduced, pressure. The resulting residue was purified by silica gel column chromatography (n-hexane/ethyl acetate), whereby Compound 27 (31.9 mg, 18%) and Compound 29 (23.9 mg, 19%) were obtained, respectively.

Compound. 27: $^1$H NMR (CDCl$_3$) δ6.24 (1H, s), 5.88 (1H, d, J=5.6 Hz), 5.31-5.76 (5H, m), 5.61 (1H, d, J=9.2 Hz), 5.33 (1H, d, J=9.4 Hz), 5.10 (1H, d, J=9.2 Hz), 3.54 (1H, d, J=9.2 Hz), 2.78-2.67 (2H, m), 2.49 (1H, m), 2.35 (1H, dd, J=13.7, 7.1 Hz), 2.16 (3H, s), 2.14 (3H, s), 2.11 (3H, s), 1.71 (3H, d, J=1.0 Hz), 1.61-1.12 (7H, m), 1.20 (3H, a, J=6.8 Hz), 1.08-0.96 (2H, m), 0.91 (3H, d, J=6.6 Hz), 0.88-0.82 (14H, m).

Compound 29: $^1$H NMR (CDCl$_3$) δ6.18 (1H, s), 5.79 (1H, a, J=5.6 Hz), 5.77 (1H, d, J=5.6 Hz), 5.74 (1H, d, J=5.6 Hz), 5.70 (1H, d, J=5.6 Hz), 5.31 (1H, d, J=9.4 Hz), 2.71-2.65 (2H, m), 2.49 (1H, m), 2.33 (1H, m), 2.11 (3H, s), 2.10 (3H, s), 1.70 (3H, d, J=1.1 Hz), 1.57-1.48 (2H, m), 1.43-1.31 (2H, m), 1.25-1.12 (3H, m), 1.17 (3H, d, J=6.8 Hz), 1.07-0.94 (2H, m), 0.90 (3H, d, J=6.6 Hz), 0.88-0.82 (14H, m).

Example 26

(2Z,4E)-2-{3-(Acetoxymethoxy)-2-methyl-3-oxopropyl}-4,6,8,10,12-pentamethyltetradec-2,4-dienoic Acid (Compound 28)

To Compound 1 (140 mg, 0.253 mmol), dichloromethane (3 mL) and triethylamine (0.3 mL, 2.15 mmol) were added, and the resulting mixture was cooled to 0° C., and then, bromomethyl acetate (0.2 mL, 2.04 mmol) was added thereto. The resulting mixture was stirred at room temperature for 1 hour. To the reaction mixture, a saturated aqueous ammonium chloride solution was added, and the resulting mixture was extracted with ethyl acetate. The organic layer was washed with saturated brine and dried over anhydrous magnesium sulfate, and then, the solvent was evaporated under reduced pressure. The resulting residue was purified by silica gel column chromatography (n-hexane/ethyl acetate), whereby Compound. 28 (27.9 mg, 24%) was obtained.

$^1$H NMR (CDCl$_3$) δ6.20 (1H, s), 5.80 (1H, d, J=5.5 Hz), 5.77 (1H, d, J=5.5 Hz), 5.31 (1H, d, J=9.4 Hz), 2.73 (1H, m), 2.65 (1H, m), 2.50 (1H, m), 2.31 (1H, dd, J=14.3, 7.8 Hz), 2.10 (3H, s), 1.71 (3H, d, J=1.1 Hz), 1.58-1.47 (2H, m), 1.44-1.30 (2H, m), 1.28-1.14 (3H, m), 1.19 (3H, d, J=7.0 Hz), 1.07-0.96 (2H, m), 0.91 (3H, d, J=6.6 Hz), 0.88-0.82 (14H, m).

Example 27

(2Z,4E)-2-[3-{4-(Acetoxymethoxy)-2-{(acetoxymethoxy)carbonyl}-1-carboxy-3-hydroxy-4-oxobutoxy}-2-methyl-3-oxopropyl]-4,6,8,10,12-pentamethyltetradec-2,4-dienoic Acid (Compound 30)

To Compound 3 (105.6 mg, 0.160 mmol), DMF (1 mL) and bromomethyl acetate (0.060 mL, 0.612 mmol) were added, and the resulting mixture was stirred at 70° C. for 1 hour. The reaction mixture was cooled to room temperature, and a saturated aqueous ammonium chloride solution was added thereto, and then, the resulting mixture was extracted with ethyl acetate. The organic layer was washed with saturated brine and dried over anhydrous sodium sulfate, and then, the solvent was evaporated under reduced pressure. The resulting residue was purified by silica gel column chromatography (chloroform/methanol), whereby Compound 30 (5.4 mg, 4.7%) was obtained.

$^1$H NMR (CDCl$_3$) δ5.96 (1H, s), 5.82-5.79 (4H, m), 5.68 (1H, d, J=3.1 Hz), 5.30 (1H, d, J=8.9 Hz), 4.72 (1H, d, J=8.5 Hz), 3.61 (1H, dd, J=8.5, 3.1 Hz), 2.87-2.69 (2H, m), 2.48 (1H, m), 2.36 (1H, m), 2.143 (3H, s), 2.139 (3H, s), 1.75 (3H, s), 1.59-1.45 (2H, m), 1.44-1.29 (2H, m), 1.24-1.13 (3H, m), 1.21 (3H, d, J=6.9 Hz), 1.08-0.91 (2H, m), 0.89 (3H, d, J=6.5 Hz), 0.86-0.81 (14H, m).

Example 28

Tris(4-acetoxybenzyl) 1-{(4Z,6E)-4-[(4-acetoxybenzyloxy)carbonyl]-2,6,8,10,12,14-hexamethylhexadec-4,6-dienoyloxy}-3-hydroxypropane-1,2,3-tricarboxylate (Compound 31)

To Compound 1 (132.2 mg, 0.239 mmol), chloroform (10 mL), 4-acetyloxybenzyl alcohol (159 mg, 0.957 mmol), DMAP (11.7 mg, 0.096 mmol), and N,N'-dicyclohexylcarbodiimide (200 mg, 0.969 mmol) were added, and the resulting mixture was stirred at room temperature for 20 hours. The insoluble matter in the reaction mixture was removed by filtration, and the solvent in the filtrate was evaporated under reduced pressure. The resulting residue was purified by silica gel column chromatography (n-hexane/ethyl acetate), whereby Compound 31 (36.5 mg, 13%) was obtained.

$^1$H NMR (CDCl$_3$) δ7.38-7.32 (8H, m), 7.10-7.04 (8H, m), 6.09 (1H, s), 5.38 (1H, d, J=9.4 Hz), 5.27 (1H, d, J=9.4 Hz), 5.14-5.04 (9H, m), 4.09 (1H, br s), 3.49 (1H, m), 2.82-2.42 (4H, m), 2.30 (3H, s), 2.29 (6H, s), 2.09 (3H, s), 1.71-1.30 (4H, m), 1.64 (3H, d, J=0.94 Hz), 1.28-0.92 (5H, m), 1.15 (3H, d, J=6.8 Hz), 0.90 (3H, d, J=6.7 Hz), 0.87-0.81 (14H, m).

Example 29

1-Methyl 5-{(S)-5-oxotetrahydrofuran-3-yl}(Z)-4-methyl-2-{(E)-2,4,6,8,10-pentamethyldodec-2-enylidene}pentanedioate (Compound 32)

In the same manner as Step 1 of Example 7, Compound 32 (3.1 mg, 52%) was obtained by using Compound 21 (5.8 mg, 0.012 mmol) and methanol (0.01 mL, 0.247 mmol), $^1$H NMR (CDCl$_3$) δ6.08 (1H, s), 5.45-5.40 (1H, m), 5.26 (1H, d, J=9.6 Hz), 4.47 (1H, dd, J=11.1, 4.9 Hz), 4.34 (1H, d, J=11.1 Hz), 3.70 (3H, s), 2.83 (1H, dd, J=18.5, 6.7 Hz), 2.72-2.63 (1H, m), 2.62-2.54 (2H, m), 2.54-2.44 (1H, m), 2.39 (1H, ddd, J=13.9, 6.6, 0.9 Hz), 1.68 (3H, d, J=0.9 Hz), 1.61-1.46 (2H, m), 1.46-1.30 (2H, m), 1.30-1.11 (3H, m), 1.17 (3H, d, J=6.9 Hz), 1.08-0.94 (2H, m), 0.90 (3H, d, J=6.6 Hz), 0.92-0.80 (14H, m).

INDUSTRIAL APPLICABILITY

According to the present invention, a 4,6-hexadecadiene-2,4-dicarboxylic acid derivative or a pharmaceutically acceptable salt thereof, each of which has an anti-tumor activity, and the like are provided.

REFERENCE TO DEPOSITED BIOLOGICAL MATERIAL

NPMD KITE BP-1377

The invention claimed is:
1. A 4,6-hexadecadiene-2,4-dicarboxylic acid derivative represented by the general formula (I) or a pharmaceutically acceptable salt thereof

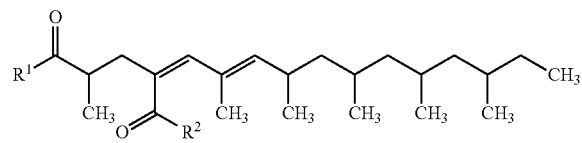

[wherein R$^4$ represents hydroxy, -OR$^3$ (wherein R$^3$ represents optionally substituted lower alkyl or an optionally substituted aliphatic heterocyclic group), or —NR$^4$R$^5$ (wherein R$^4$ and R$^5$ may be the same or different, and each represents a hydrogen atom or optionally substituted lower alkyl) and
R$^2$ represents hydroxy or —OR$^6$ (wherein R$^6$ represents optionally substituted lower alkyl or optionally substituted aralkyl)].

2. The 4,6-hexadecadiene-2,4-dicarboxylic acid derivative or a pharmaceutically acceptable salt thereof according to claim 1, wherein R$^2$ is hydroxy.

3. The 4,6-hexadecadiene-2,4-dicarboxylic acid derivative or a pharmaceutically acceptable salt thereof according to claim 1, wherein R$^2$ is —OR$^6$ (wherein R$^6$ represents optionally substituted lower alkyl or optionally substituted aralkyl).

4. The 4,6-hexadecadiene-2,4-dicarboxylic acid derivative or a pharmaceutically acceptable salt thereof according to claim 3, wherein R$^6$ is optionally substituted lower alkyl.

5. The 4,6-hexadecadiene-2,4-dicarboxylic acid derivative or a pharmaceutically acceptable salt thereof according to claim 3, wherein R$^6$ is substituted lower alkyl.

6. The 4,6-hexadecadiene-2,4-dicarboxylic acid derivative or a pharmaceutically acceptable salt thereof according to claim 3, wherein $R^6$ is acetoxymethyl.

7. The 4,6-hexadecadiene-2,4-dicarboxylic acid derivative or a pharmaceutically acceptable salt thereof according to claim 1, wherein $R^2$ is hydroxy.

8. The 4,6-hexadecadiene-2,4-dicarboxylic acid derivative or a pharmaceutically acceptable salt thereof according to claim 1, wherein $R^2$ is -$OR^3$ (wherein $R^3$ represents optionally substituted lower alkyl or an optionally substituted aliphatic heterocyclic group).

9. The 4,6-hexadecadiene-2,4-dicarboxylic acid derivative or a pharmaceutically acceptable salt thereof according to claim 8, wherein $R^3$ is an optionally substituted aliphatic heterocyclic group.

10. The 4,6-hexadecadiene-2,4-dicarboxylic acid derivative or a pharmaceutically acceptable salt thereof according to claim 8, wherein $R^3$ is optionally substituted tetrahydrofuranyl.

11. The 4,6-hexadecadiene-2,4-dicarboxylic acid derivative or a pharmaceutically acceptable salt thereof according to claim 8, wherein $R^3$ is optionally substituted oxotetrahydrofuranyl.

12. The 4,6-hexadecadiene-2,4-dicarboxylic acid derivative or a pharmaceutically acceptable salt thereof according to claim 8, wherein $R^3$ is oxotetrahydrofuranyl substituted with carboxy.

13. The 4,6-hexadecadiene-2,4-dicarboxylic acid derivative or a pharmaceutically acceptable salt thereof according to claim 8, wherein $R^3$ is optionally substituted lower alkyl.

14. The 4,6-hexadecadiene-2,4-dicarboxylic acid derivative or a pharmaceutically acceptable salt thereof according to claim 8, wherein $R^3$ is substituted lower alkyl.

15. The 4,6-hexadecadiene-2,4-dicarboxylic acid derivative or a pharmaceutically acceptable salt thereof according to claim 8, wherein $R^3$ is substituted propyl.

16. The 4,6-hexadecadiene-2,4-dicarboxylic acid derivative or a pharmaceutically acceptable salt thereof according to claim 1, wherein the 4,6-hexadecadiene-2,4-dicarboxylic acid derivative is selected from 4-{(4Z,6E)-4-carboxy-2,6,8,10,12,14-hexamethylhexadec-4,6-dienoyloxy}-5-oxotetrahydrofuran-2,3-dicarboxylic acid and 1-{(4Z,6E)-4-carboxy-2,6,8,10,12,14-hexamethylhexadec-4,6-dienoyloxy}-3-hydroxypropane-1,2,3-tricarboxylic acid.

17. A pharmaceutical composition comprising, as an active ingredient, the 4,6-hexadecadiene-2,4-dicarboxylic acid derivative or a pharmaceutically acceptable salt thereof according to claim 1.

18. A method for inhibiting the growth of cervical cancer cells comprising a step of administering an effective amount of the 4,6-hexadecadiene-2,4-dicarboxylic acid derivative or a pharmaceutically acceptable salt thereof according to claim 1.

* * * * *

UNITED STATES PATENT AND TRADEMARK OFFICE
CERTIFICATE OF CORRECTION

PATENT NO.       : 9,260,459 B2
APPLICATION NO.  : 14/409308
DATED            : February 16, 2016
INVENTOR(S)      : Shimpei Yamaguchi et al.

It is certified that error appears in the above-identified patent and that said Letters Patent is hereby corrected as shown below:

In the Claims

At column 40, claim number 1, line number 46, change $R^4$ to $R^1$.

Signed and Sealed this
Tenth Day of May, 2016

Michelle K. Lee
*Director of the United States Patent and Trademark Office*